United States Patent
Kashima et al.

(10) Patent No.: US 11,154,179 B2
(45) Date of Patent: Oct. 26, 2021

(54) MEDICAL IMAGE PROCESSING APPARATUS, MEDICAL IMAGE PROCESSING SYSTEM, AND DRIVING METHOD OF MEDICAL IMAGE PROCESSING APPARATUS

(71) Applicant: Sony Corporation, Tokyo (JP)

(72) Inventors: Koji Kashima, Kanagawa (JP); Takeshi Miyai, Kanagawa (JP)

(73) Assignee: SONY CORPORATION, Tokyo (JP)

(*) Notice: Subject to any disclaimer, the term of this patent is extended or adjusted under 35 U.S.C. 154(b) by 0 days.

(21) Appl. No.: 16/640,730

(22) PCT Filed: Jul. 31, 2018

(86) PCT No.: PCT/JP2018/028551
§ 371 (c)(1),
(2) Date: Feb. 21, 2020

(87) PCT Pub. No.: WO2019/044328
PCT Pub. Date: Mar. 7, 2019

(65) Prior Publication Data
US 2020/0178760 A1    Jun. 11, 2020

(30) Foreign Application Priority Data
Aug. 31, 2017  (JP) .............................. JP2017-166591

(51) Int. Cl.
*A61B 1/00*    (2006.01)
*A61L 2/07*    (2006.01)
(Continued)

(52) U.S. Cl.
CPC .......... *A61B 1/00009* (2013.01); *A61B 1/123* (2013.01); *A61L 2/07* (2013.01);
(Continued)

(58) Field of Classification Search
CPC ............................ A61B 1/0009; G06T 5/003
See application file for complete search history.

(56) References Cited

U.S. PATENT DOCUMENTS

| | | | | |
|---|---|---|---|---|
| 5,534,221 A | * | 7/1996 | Hillebrenner | A61B 1/125 206/438 |
| 5,868,664 A | * | 2/1999 | Speier | A61B 1/042 600/112 |

(Continued)

FOREIGN PATENT DOCUMENTS

| | | |
|---|---|---|
| JP | 2000-139819 A | 5/2000 |
| JP | 2007-097652 A | 4/2007 |
| JP | 2009-285191 A | 12/2009 |

OTHER PUBLICATIONS

Extended European Search Report dated Jun. 8, 2020 in European Application No. 18849540.2.

(Continued)

*Primary Examiner* — Irfan Habib
(74) *Attorney, Agent, or Firm* — Xsensus LLP

(57) ABSTRACT

Control of expansion of a depth of field using a birefringent mask is realized in a more preferred aspect.
A medical image processing apparatus includes a control unit that performs control so as to generate a corrected image by executing image processing on an image obtained by imaging a subject image of a patient acquired via an optical system including a birefringent mask and an acquisition unit that acquires information regarding an application situation of high-pressure steam sterilization processing on the optical system, in which the control unit controls the image processing according to the application situation of the high-pressure steam sterilization processing.

18 Claims, 15 Drawing Sheets

(51) Int. Cl.
*G02B 5/30* (2006.01)
*A61B 1/12* (2006.01)
*G02B 27/00* (2006.01)
*G06T 5/00* (2006.01)

(52) U.S. Cl.
CPC ....... *G02B 5/3083* (2013.01); *G02B 27/0075* (2013.01); *G06T 5/003* (2013.01); *A61B 2562/0271* (2013.01); *A61L 2202/14* (2013.01); *A61L 2202/24* (2013.01); *G06T 2207/10068* (2013.01)

(56) References Cited

U.S. PATENT DOCUMENTS

| | | | | | |
|---|---|---|---|---|---|
| 8,034,193 | B2* | 10/2011 | Suzuki | ................... | A61B 90/70 134/166 C |
| 8,176,771 | B2* | 5/2012 | Onishi | ............... | A61B 1/00057 73/45.5 |
| 8,972,714 | B2* | 3/2015 | Talbert | ...................... | H04L 9/32 713/150 |
| 9,089,255 | B2* | 7/2015 | Kato | .................. | A61B 1/00124 |
| 9,277,850 | B2* | 3/2016 | Kubach | ................... | G01M 3/26 |
| 9,936,859 | B2* | 4/2018 | Ebata | ............... | A61B 17/00234 |
| 10,350,318 | B2* | 7/2019 | Sharma | ..................... | A61L 2/07 |
| 2001/0033806 | A1* | 10/2001 | Stanley | .................. | A61B 1/123 422/28 |
| 2005/0065402 | A1* | 3/2005 | Moriyama | ................ | A61L 2/07 600/133 |
| 2005/0148819 | A1* | 7/2005 | Noguchi | ............ | A61B 1/00059 600/133 |
| 2006/0263245 | A1* | 11/2006 | Watanabe | .............. | A61B 1/121 422/400 |
| 2013/0174042 | A1* | 7/2013 | Kim | ......................... | G06F 8/65 715/735 |
| 2015/0085186 | A1* | 3/2015 | Amling | .................. | H04N 21/47 348/383 |
| 2016/0381278 | A1* | 12/2016 | Kang | .................... | H04N 5/265 348/68 |

OTHER PUBLICATIONS

International Search Report and Written Opinion dated Oct. 16, 2018 for PCT/JP2018/028551 filed on Jul. 31, 2018, 10 pages including English Translation of the International Search Report.

* cited by examiner

FIG. 2
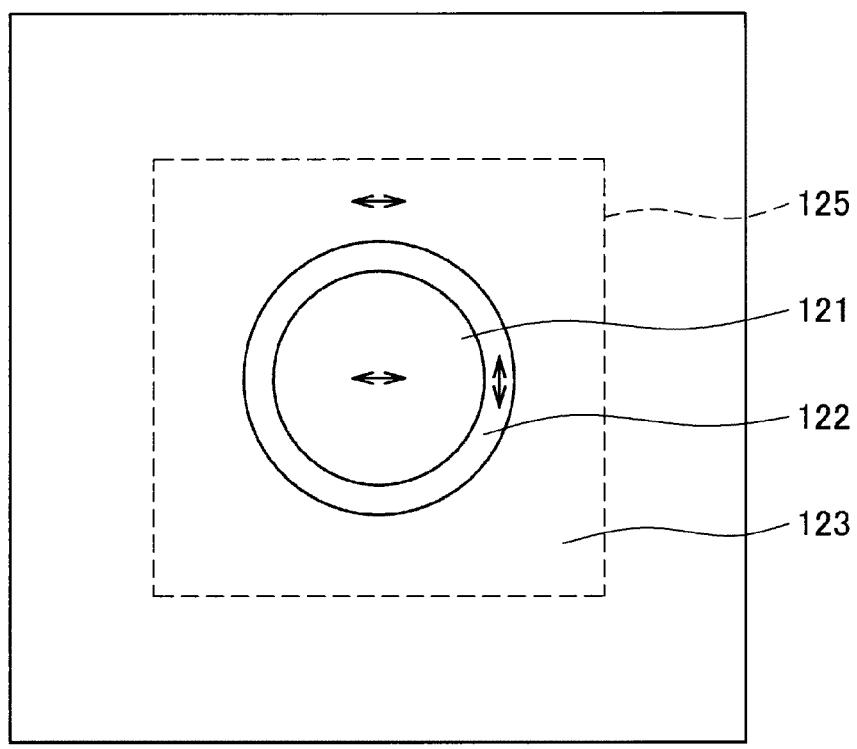
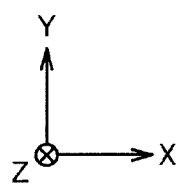

MEDICAL IMAGE PROCESSING APPARATUS, MEDICAL IMAGE PROCESSING SYSTEM, AND DRIVING METHOD OF MEDICAL IMAGE PROCESSING APPARATUS

CROSS-REFERENCE TO RELATED APPLICATIONS

The present application is based on PCT filing PCT/JP2018/028551, filed Jul. 31, 2018, which claims priority to JP 2017-166591, filed Aug. 31, 2017, the entire contents of each are incorporated herein by reference.

TECHNICAL FIELD

The present disclosure relates to a medical image processing apparatus, a medical image processing system, and a driving method of the medical image processing apparatus.

BACKGROUND ART

In recent years, with development in surgical techniques and surgical tools, surgical (so-called microsurgery) in which various treatments are applied while observing an affected part by a medical observation device such as a surgical microscope, an endoscope, or the like has been frequently performed. Furthermore, among such medical observation devices, a device has been proposed which makes a display device such as a monitor display an image of an affected part captured by an imaging device (camera) and the like as an electronic image, in addition to the device that can optically observe the affected part. For example, Patent Document 1 discloses an example of a so-called electronic endoscope system that can make a display unit display an image of an affected part captured by an imaging device.

Furthermore, in recent years, application of various technologies for further improving image quality of an image to be captured to a system to which the medical observation device is applied has been examined. As such a technology, a technology for expanding a depth of field referred to as Extended Depth Of Field (EDOF) has attracted attention. As a specific example of the EDOF technology, a method is exemplified for expanding the depth of field by applying the birefringent mask to the optical system that acquires the subject image and applying the image processing (image signal processing) on the image captured via the optical system according to the optical characteristics of the birefringent mask.

CITATION LIST

Patent Document

Patent Document 1: Japanese Patent Application Laid-Open No. 2009-285191

SUMMARY OF THE INVENTION

Problems to be Solved by the Invention

On the other hand, in the medical field, a situation may be assumed in which autoclave (high-pressure steam) sterilization processing is executed on a medical device such as an endoscope each time when the device is used. There is a case where, by repeatedly executing such autoclave sterilization processing, the optical characteristics of the birefringent mask applied to the optical system such as the endoscope change, and the change has an effect on an image obtained as a result of the processing regarding the expansion of the depth of field (for example, image quality of image changes) (for example, image processing described above).

Therefore, the present disclosure proposes a technology that can realize control of expansion of a depth of field using a birefringent mask in a more preferred aspect.

Solutions to Problems

According to the present disclosure, a medical image processing apparatus is provided that includes a control unit that performs control so as to generate a corrected image by executing image processing on an image obtained by imaging a subject image of a patient acquired via an optical system including a birefringent mask and an acquisition unit that acquires information regarding an application situation of high-pressure steam sterilization processing on the optical system, in which the control unit controls the image processing according to the application situation of the high-pressure steam sterilization processing.

Furthermore, according to the present disclosure, a medical image processing system is provided that includes an imaging device including an optical system that includes a birefringent mask and acquires a subject image of a patient and an imaging unit that captures an image of the subject image and an image processing device including a control unit that performs control so as to generate a corrected image by executing image processing on the image captured by the imaging unit and an acquisition unit that acquires information regarding an application situation of high-pressure steam sterilization processing on the optical system, in which the control unit controls the image processing according to the application situation of the high-pressure steam sterilization processing.

Furthermore, according to the present disclosure, a driving method of a medical image processing apparatus by a computer is provided that includes performing control so as to generate a corrected image by executing image processing on an image obtained by imaging a subject image of a patient acquired via an optical system including a birefringent mask and acquiring information regarding an application situation of high-pressure steam sterilization processing on the optical system, in which the image processing is controlled according to the application situation of the high-pressure steam sterilization processing.

Effects of the Invention

As described above, according to the present disclosure, a technology that can realize control of expansion of a depth of field using a birefringent mask in a more preferred aspect is provided.

Note that the above effects are not necessarily limited, and any effect that has been described in the present specification or other effect which may be found from the present specification may be obtained together with or instead of the above effects.

BRIEF DESCRIPTION OF DRAWINGS

FIG. 2 is an explanatory diagram for explaining an example of a schematic configuration of an optical element applied to an endoscope according to the embodiment.

MODE FOR CARRYING OUT THE INVENTION

Figure 1:
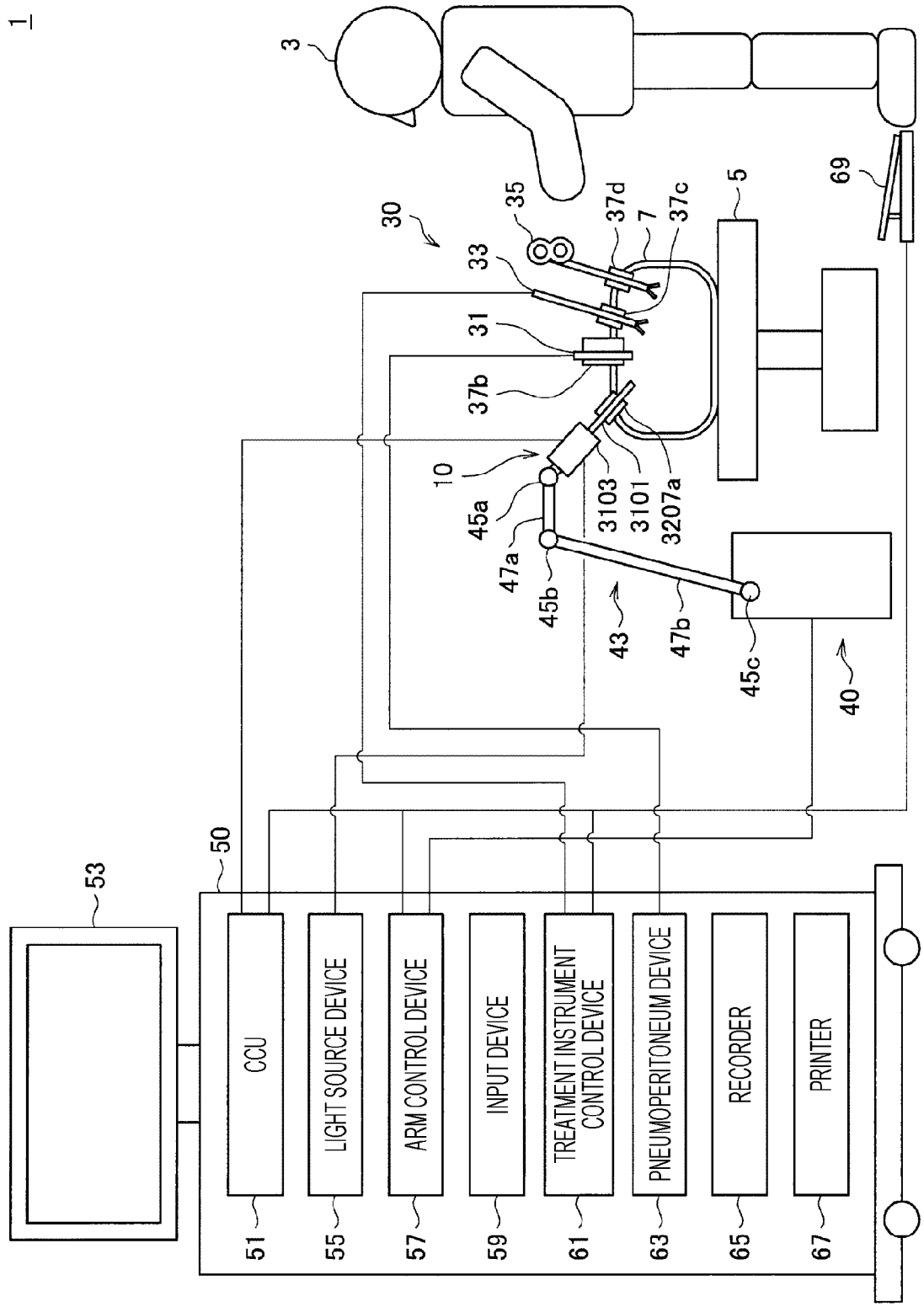
FIG. 1 is an explanatory diagram for explaining an example of a schematic configuration of a medical image processing system according to one embodiment of the present disclosure.

Hereinafter, preferred embodiments of the present disclosure will be described in detail with reference to the accompanying drawings. Note that, in the present specification and the drawings, components having substantially the same functional configuration are denoted with the same reference numeral so as to omit redundant description.

Note that the description will be made in the following order.

1. Outline of System
2. Configuration of Optical Element
3. Study on EDOF Technology Using Birefringent Mask
4. Technical Features
4.1. Summary
4.2. Functional Configuration
4.3. Processing
4.4. Modification
5. Hardware Configuration
6. Application Example
7. Conclusion

1. Outline of System

First, an outline of an exemplary system to which the technology according to the present disclosure may be applied will be described. FIG. 1 is an explanatory diagram for explaining an example of a schematic configuration of a medical image processing system according to one embodiment of the present disclosure. A medical image processing system 1 is an endoscopic surgery system. In the example in FIG. 1, an operator (surgeon) 3 performs an endoscopic surgery on a patient 7 on a patient bed 5 by using the medical image processing system 1. The medical image processing system 1 includes an endoscope 10, other surgical tools (surgical instrument) 30, a support arm device 40 that supports the endoscope 10, and a cart 50 on which various devices for an endoscopic surgery are mounted.

In the endoscopic surgery, instead of cutting an abdominal wall and opening an abdomen, the abdominal wall is punctured by a plurality of cylindrical puncture devices 37a to 37d referred to as trocars. Then, through the trocars 37a to 37d, a lens barrel 11 of the endoscope 10 and the other surgical instruments 30 are inserted into a body cavity of the patient 7. In the example in FIG. 1, as the other surgical instruments 30, a pneumoperitoneum tube 31, an energy treatment instrument 33, and a forceps 35 are illustrated. The energy treatment instrument 33 is used for treatment such as tissue incision or detachment or blood vessel sealing with a high-frequency current or ultrasonic vibration. Note that the illustrated surgical instruments 30 are merely an example, and other types of surgical instruments (for example, tweezers or retractor) may be used.

An image in the body cavity of the patient 7 imaged by the endoscope 10 is displayed by a display device 53. While viewing a display image in real time, the operator 3 performs processing, for example, for removing an affected part by using the energy treatment instrument 33 and the forceps 35. Note that, although not illustrated, the pneumoperitoneum tube 31, the energy treatment instrument 33, and the forceps 35 are supported by a user such as the operator 3 or an assistant during the surgery.

The support arm device 40 includes an arm portion 43 extending from a base portion 41. In the example in FIG. 1, the arm portion 43 includes joint portions 45a, 45b, and 45c and links 47a and 47b and supports the endoscope 10. The arm portion 43 is driven according to control from an arm control device 57. As a result, a position and a posture of the endoscope 10 are controlled, and the endoscope 10 may be stably fixed at the position.

The endoscope 10 includes the lens barrel 11 and a camera head 13 connected to a base end of the lens barrel 11. A part of the lens barrel 11 from the front end to a certain position is inserted into the body cavity of the patient 7. In the example in FIG. 1, the endoscope 10 is configured as a so-called rigid scope having the rigid lens barrel 11. However, the endoscope 10 may be configured as a so-called flexible scope.

At the front end of the lens barrel 11, an opening in which an objective lens is fitted is provided. A light source device 55 is connected to the endoscope 10, and light generated by the light source device 55 is guided to the front end of the lens barrel by a light guide extending in the lens barrel 11 and is emitted to an object to be observed in the body cavity of the patient 7 through the objective lens. Note that the endoscope 10 may be a forward-viewing endoscope, an oblique-viewing endoscope, or a side-viewing endoscope.

The camera head 13 includes an irradiation unit, an optical system, a drive system, and an imaging unit which incorporates an image sensor. The irradiation unit irradiates a subject with irradiation light supplied from the light source device 55 through the light guide. The optical system typically includes a lens unit and collects observation light from the subject taken from the front end of the lens barrel 11 (reflected light of irradiation light) toward the image sensor. Positions of a zoom lens and a focus lens in the lens unit may be driven and changed by the drive system so as to variably control imaging conditions such as magnification or a focal length. The image sensor of the camera head 13 photoelectrically converts the observation light collected by the optical system and generates an image signal which is an electrical signal. The image sensor may be a three-plate sensor having separate imaging elements which respectively generate image signals having three color components or may be other type of image sensor such as a single-plate or two-plate sensor. The image sensor may include any type of imaging element, for example, a Complementary Metal Oxide Semiconductor (CMOS), a Charge-Coupled Device (CCD), or the like. The image signal generated by the image sensor is transmitted to a camera control unit (CCU) 51 as RAW data.

In an embodiment, a captured image expressed by the image signal generated by the camera head 13 includes a parallax determination image. The parallax determination image typically includes a right-eye image and a left-eye image. The right-eye image and the left-eye image may be respectively generated by a right-eye image sensor and a left-eye image sensor of a compound eye camera. Alternatively, the right-eye image and the left-eye image may be generated by a single image sensor of a monocular camera (for example, by shutter switching method).

The CCU 51 is connected to the camera head 13 via a signal line and a communication interface. The signal line between the camera head 13 and the CCU 51 is a high-speed transmission line that enables bidirectional communication, for example, an optical cable and the like. The CCU 51 includes a processor such as a Central Processing Unit (CPU) and a memory such as a Random Access Memory (RAM) and comprehensively controls operations of the endoscope 10 and the display device 53. The CCU 51 may further include a frame memory for temporarily storing the image signal and one or more Graphics Processing Units (GPU) that execute image processing. For example, the CCU 51 determines a parallax for each pixel (or for each other unit) on the basis of the parallax determination image input from the camera head 13. The parallax to be determined may be used for image processing, for example, generation of a stereoscopic image, expansion of the depth of field, emphasize on a stereoscopic effect, or expansion of a dynamic range. The CCU 51 may output an image generated as a result of the image processing to the display device 53 to be displayed or to a recorder 65 for recording. A series of output images may constitute a moving image (video). The image processing executed by the CCU 51 may include general processing, for example, development, noise reduction, or the like. Furthermore, the CCU 51 transmits a control signal to the camera head 13 and controls driving of the camera head 13. The control signal may include, for example, information for specifying the imaging conditions described above.

The display device 53 displays an image based on the input display image signal according to the control from the CCU 51. Furthermore, the display device 53 may display a stereoscopic image on the basis of the input display image signal. In this case, the display device 53 may display the stereoscopic image by any method such as an active shutter method, a passive method, or a glassless method.

The light source device 55 includes, for example, an LED, a xenon lamp, a halogen lamp, a laser light source, or a light source corresponding to a combination of these and supplies irradiation light to emitted to an observation target to the endoscope 10 through the light guide.

The arm control device 57 includes a processor, for example, a CPU and the like and controls driving of the arm portion 43 of the support arm device 40 by operating according to a predetermined program.

An input device 59 includes one or more input interfaces that accept a user input to the medical image processing system 1. A user can input various information or various instructions to the medical image processing system 1 via the input device 59. For example, the user may input setting information to be described later or other parameters via the input device 59. Furthermore, for example, the user inputs an instruction to drive the arm portion 43, an instruction to change the imaging conditions (type of irradiation light, magnification, focal length, and the like) of the endoscope 10, an instruction to drive the energy treatment instrument 33, or the like via the input device 59.

The input device 59 may handle any type of user inputs. For example, the input device 59 may detect a physical user input via a mechanism such as a mouse, a keyboard, a switch (for example, foot switch 69), a lever, or the like. The input device 59 may detect a touch input via a touch panel. The input device 59 may be realized in a form of a wearable device such as a glass-shaped device or a Head Mounted Display (HMD) and may detect a user's line-of-sight and a gesture. Furthermore, the input device 59 includes a microphone that can collect voice of the user and may detect a voice command via the microphone.

A treatment instrument control device 61 controls driving of the energy treatment instrument 33 for treatments such as cauterization or incision of tissue, blood vessel sealing, or the like. In order to secure a field of view observed by the endoscope 10 and a working space of the operator, a pneumoperitoneum device 63 injects gas into the body cavity via the pneumoperitoneum tube 31 to swell the body cavity of the patient 7. The recorder 65 records various information related to medical works (for example, one or more of setting information, image information, measurement information from vital sensor (not illustrated)) to a recording medium. A printer 67 prints various information related to the medical works in any format such as a text, an image, or a graph.

Note that the endoscope 10 according to the present embodiment may be configured so that an optical element 12 such as a so-called optical mask may be inserted between the lens barrel 11 and the camera head 13. Examples of the optical element 12 include, for example, a Birefringent Mask (BM), a three-dimensional phase mask (Cubic Phase Mask), and the like. In the medical image processing system 1 according to the present embodiment, by interposing such an optical element 12 between the lens barrel 11 and the camera head 13, optical characteristics of a series of optical systems that form a subject image with respect to the imaging element in the camera head 13 are changed, and an amount of blur of an image to be captured is adjusted (for example, control depth of field). Note that the optical element 12 will be separately described later in detail.

The outline of the exemplary system to which the technology according to the present disclosure may be applied has been described above with reference to FIG. 1.

2. Configuration of Optical Element

Subsequently, features of the optical element 12 which is inserted between the lens barrel 11 and the camera head 13 in the endoscope 10 according to the present embodiment will be described in detail with reference to FIGS. 2 to 6.

In recent years, a resolution of an imaging element (so-called image sensor) used for an imaging device such as a camera tends to be higher, and the imaging element is not limited to an imaging element having "HD (1280×720)", and imaging elements having "4K UHD (3840×2160)" and "8K UHD (7680×4320)" have been proposed. Therefore, even in a medical observation device (imaging device) such as the endoscope 10 according to the present embodiment, it is desired to increase the resolution of the image to be captured. On the other hand, a pixel size of the imaging element tends to be reduced as the resolution is increased, and an amount of light collected by each pixel relatively tends to be smaller. Under such a situation, for example, there is a case where an insufficient light amount is compensated by opening an aperture (that is, reduce F value). However, there is a case where the depth of field becomes narrower as the aperture is opened.

In consideration of the above situation, for example, there is a case where a technology called Extended Depth of Field (EDOF), which expands the depth of field, is applied. In the endoscope 10 according to the present embodiment, the depth of field of the image to be captured is further expanded by applying the EDOF technology using the birefringent mask among the EDOF technology. Specifically, the endoscope 10 according to the present embodiment is configured so that the optical element 12 can be inserted between the lens barrel 11 and the camera head 13 as described above, and the depth of field of the image to be captured is controlled by inserting the optical element 12.

For example, FIG. 2 is an explanatory diagram for explaining an example of a schematic configuration of the optical element 12 to which the endoscope 10 according to the present embodiment is applied. Specifically, FIG. 2 illustrates an example in a case where the optical element 12 is configured as a birefringent mask and illustrates an example of the configuration of the optical element 12 in a case where the optical element 12 is viewed from an optical axis direction of a camera head. Note that, in FIG. 2, the horizontal direction of the drawing is the x direction, the vertical direction is the y direction, and the depth direction (that is, optical axis direction of camera head 13) is the z direction. Furthermore, in the following description, unless otherwise defined, the optical axis direction (in other words, depth direction) of the imaging device (for example, imaging device 3) is the z direction, and the horizontal direction and the vertical direction of the image to be captured by the imaging device (that is, directions perpendicular to optical axis) are respectively the x direction and the y direction.

As illustrated in FIG. 2, in the optical element 12, a plurality of polarization elements 121 to 123 is arranged in a region indicated by a reference numeral 125 from the vicinity of the center of the region 125 toward the outside. As a more specific example, in the example illustrated in FIG. 2, in the optical element 12, the plurality of polarization elements 121 to 123 is concentrically arranged on an xy plane perpendicular to the optical axis. Note that, an arrow illustrated in FIG. 2 schematically indicates a polarization direction of the polarization element to which the arrow is applied. That is, the polarization elements 121 to 123 are provided so that the polarization directions of the adjacent polarization elements are different from each other.

For example, in the example illustrated in FIG. 2, the polarization direction of the polarization element 121 is the x direction. Whereas, the polarization direction of the polarization element 122 adjacent to the polarization element 121 is the y direction and is a direction rotated by 90 degrees with respect to the polarization direction (x direction) of the polarization element 121. Similarly, the polarization direction of the polarization element 123 adjacent to the polarization element 122 is the x direction and is a direction rotated by 90 degrees with respect to the polarization direction (y direction) of the polarization element 122.

With such a configuration, the light collected by the lens barrel 11 enters any one of the polarization elements 121 to 123 of the optical element 12 according to the position on the xy plane perpendicular to the optical axis (z direction), and the light polarized by the polarization element enters the camera head 13.

Figure 3:
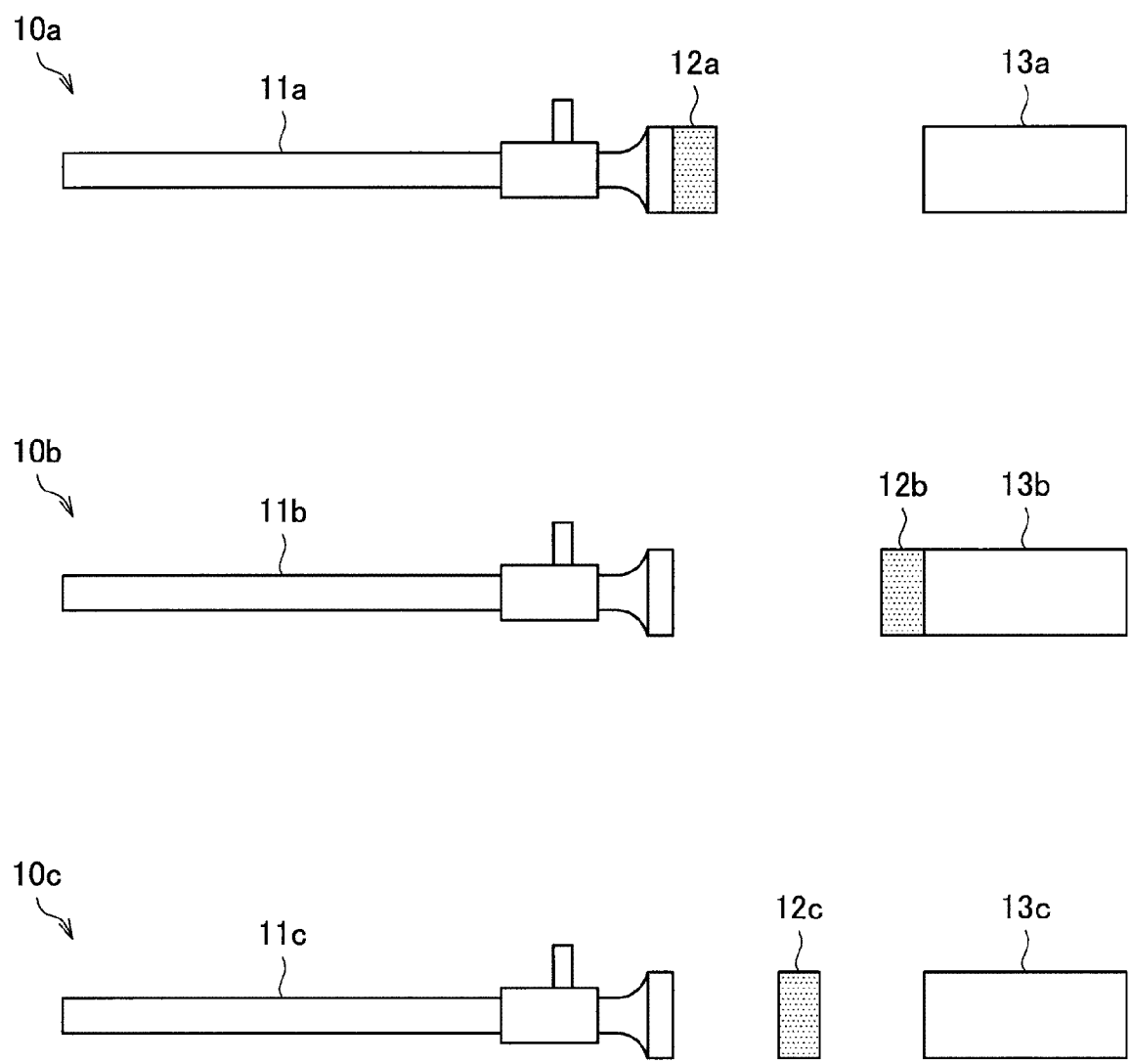
FIG. 3 is an explanatory diagram for explaining an example of a configuration of the endoscope according to the embodiment.

Note that if the optical element 12 can be interposed between the lens barrel 11 and the camera head 13, the configuration of the endoscope 10 is not particularly limited. For example, FIG. 3 is an explanatory diagram for explaining an example of the configuration of the endoscope 10 according to the present embodiment and illustrates an example of the configuration which makes the optical element 12 be interposed between the lens barrel 11 and the camera head 13.

As a specific example, an exemplary configuration of an endoscope indicated by a reference numeral 10a is an example in a case where the optical element 12 is configured as a part of the lens barrel 11. Specifically, in the endoscope 10a, an optical element 12a is held by an end of a lens barrel 11a on a side attached to a camera head 13a. With such a configuration, light collected by the lens barrel 11a passes through the optical element 12a when being emitted to the outside of the lens barrel 11a, and the light that has passed through the optical element 12a enters the camera head 13a. With such a configuration, depth of field expansion processing optimal for the endoscope can be executed.

Furthermore, as another example, an exemplary configuration of an endoscope indicated by a reference numeral 10b is an example in a case where the optical element 12 is configured as a part of the camera head 13. Specifically, in an endoscope 10b, an optical element 12a is held by an end of a camera head 13b on the side attached to a lens barrel 11b. With such a configuration, light collected by the lens barrel 11b passes through the optical element 12b when entering the camera head 13b. With such a configuration, the depth of field expansion processing can be executed by using a conventional endoscope, not a dedicated endoscope.

Furthermore, an exemplary configuration of an endoscope indicated by a reference numeral 10c is an example in a case where the optical element 12 is configured as a so-called attachment. Specifically, the optical element 12 is configured to be removable from a lens barrel 11c and a camera head 13c so as to be interposed between the lens barrel 11c and the camera head 13c. With such a configuration, by attaching the optical element 12c to be interposed between the lens barrel 11c and the camera head 13c, light collected by the lens barrel 11c enters the camera head 13c after passing through the optical element 12c. With such a configuration, since the optical element can be used for various endoscopes and camera heads, it is easy to introduce the optical element.

Of course, the exemplary configurations illustrated in FIG. 3 are merely examples. It goes without saying that the configuration of the endoscope 10 is not limited to only the exemplary configurations illustrated in FIG. 3 if the optical element 12 can be interposed between the lens barrel 11 and the camera head 13.

Figure 4:
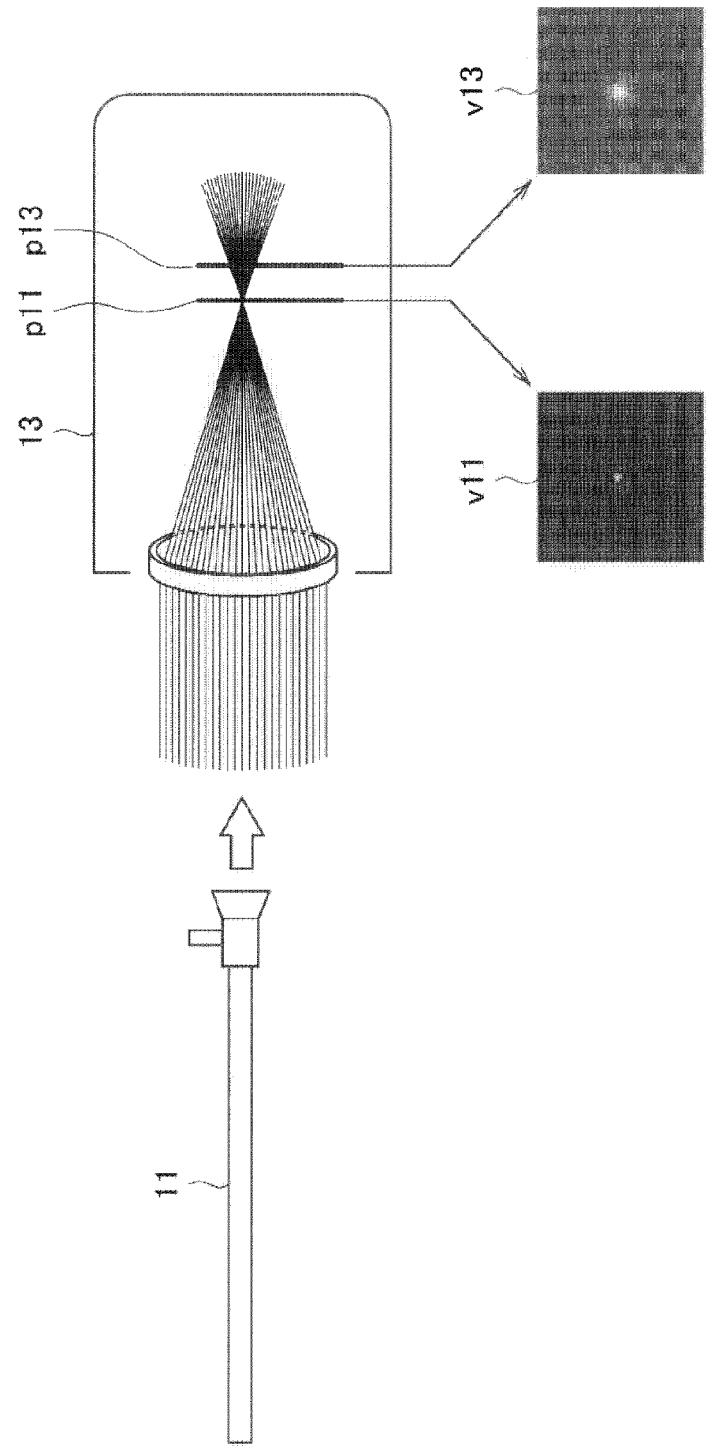
FIG. 4 is an explanatory diagram for explaining characteristics of the optical element according to the embodiment.
Figure 5:
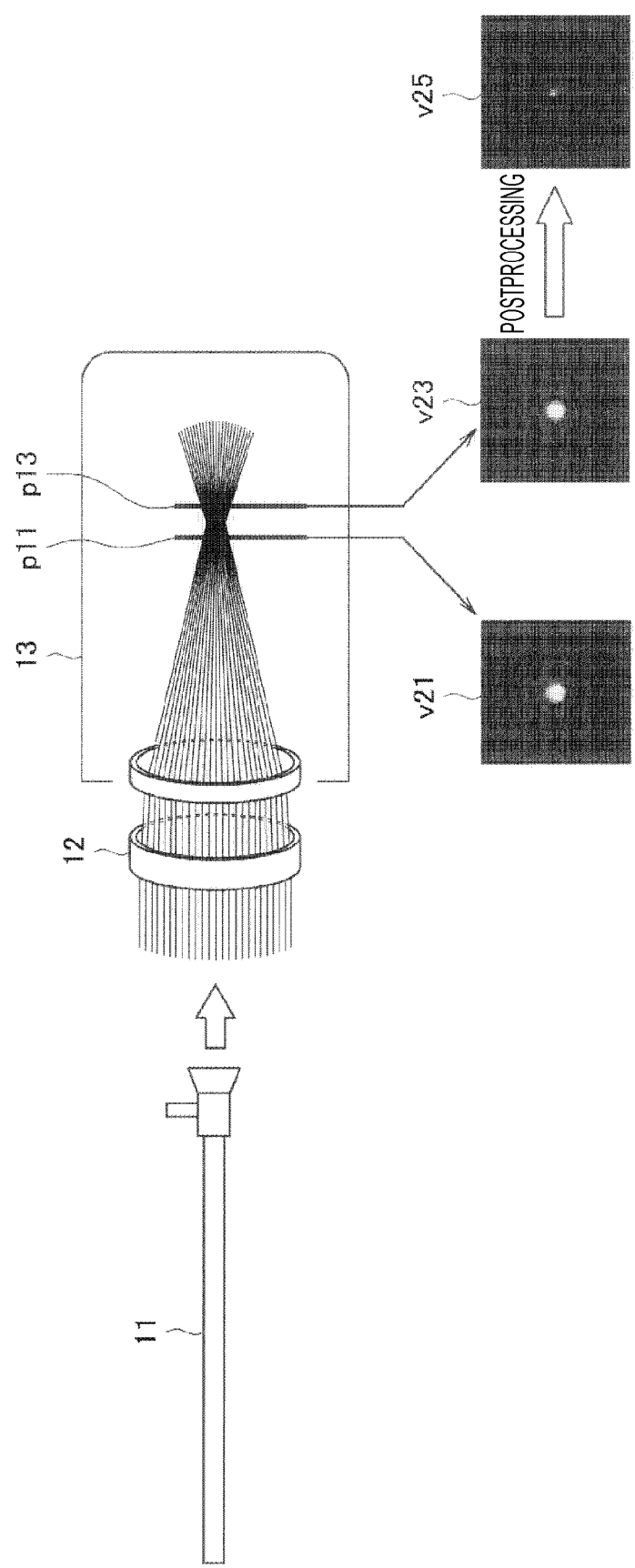
FIG. 5 is an explanatory diagram for explaining the characteristics of the optical element according to the embodiment.

Here, the characteristics of the optical element 12 illustrated in FIG. 2 will be described with reference to FIGS. 4 and 5. FIGS. 4 and 5 are explanatory diagrams for explaining the characteristics of the optical element 12 according to the present embodiment. Specifically, FIG. 4 is an example in a case where the optical element 12 is not interposed between the lens barrel 11 and the camera head 13 and schematically illustrates an optical path of light collected by the lens barrel 11 and guided to the camera head 13. Furthermore, FIG. 5 is an example in a case where the optical element 12 is interposed between the lens barrel 11 and the camera head 13 and schematically illustrates an optical path of light collected by the lens barrel 11 and guided to the camera head 13 via the optical element 12.

In the example illustrated in FIG. 4, the optical path of the light collected by the lens barrel 11 and guided to the camera head 13 is controlled to form an image on an imaging surface of the imaging element by an image formation optical system of the camera head 13. In FIG. 4, an image indicated by a reference numeral vii schematically illustrates a subject image formed at a position indicated by a reference numeral p11. Furthermore, an image indicated by a reference numeral v13 schematically illustrates a subject image formed at a position indicated by a reference numeral p13.

On the other hand, in the example illustrated in FIG. 5, the light collected by the lens barrel 11 is guided to the camera head 13 via the optical element 12, and the optical path is controlled by the image formation optical system of the camera head 13. In FIG. 5, an image indicated by a reference numeral v21 schematically illustrates a subject image formed at a position indicated by a reference numeral p11. Furthermore, an image indicated by a reference numeral v23 schematically illustrates a subject image formed at a position indicated by a reference numeral p13.

As can be understood by comparing FIGS. 4 and 5, the insertion of the optical element 12 changes the characteristics of the series of optical systems to form the subject image on the imaging element of the camera head 13 (hereinafter, simply referred to as "a series of optical systems"). Specifically, as the optical element 12 is inserted, a change in an image formation shape of the subject image (that is, Point Spread Function (PSF)) between the positions p11 and p13 is smaller than that before the insertion of the optical element 12.

Figure 6:
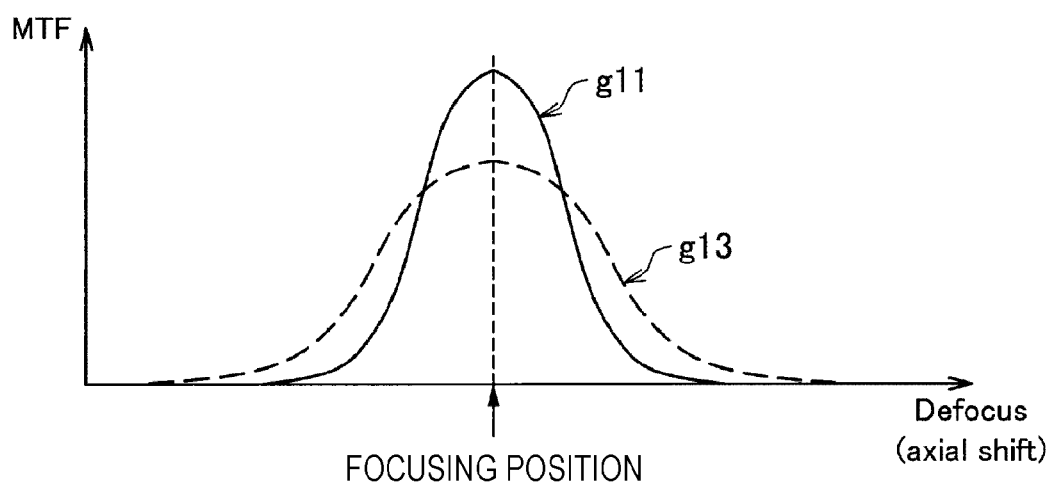
FIG. 6 is an explanatory diagram for explaining an example of the characteristics of the optical element applied to the endoscope according to the embodiment.

For example, FIG. 6 is an explanatory diagram for explaining an example of the characteristics of the optical element 12 applied to the endoscope 10 according to the present embodiment and illustrates an example of a change in a Modulation Transfer Function (MTF) of the series of optical systems in accordance with the insertion of the optical element 12. In FIG. 6, the horizontal axis indicates a deviation (that is, defocus amount) in the optical axis direction with respect to the image forming plane (in other words, focusing position) of the series of optical systems, and the vertical axis indicates a modulation transfer function (MTF). Furthermore, in FIG. 6, a graph indicated by a reference numeral g11 illustrates an example of a modulation transfer function (MTF) of the series of optical systems in a case where the optical element 12 is not interposed between the lens barrel 11 and the camera head 13 as illustrated in FIG. 4. Furthermore, a graph indicated by a reference numeral g13 illustrates an example of a modulation transfer function (MTF) of the series of optical systems in a case where the optical element 12 is inserted between the lens barrel 11 and the camera head 13 as illustrated in FIG. 5.

As illustrated in FIG. 6, by applying the optical element 12, the characteristics of the series of optical systems change so that the modulation transfer function (MTF) is distributed across a wider range along the optical axis direction than that before application of the optical element 12. That is, the application of the optical element 12 can expand the depth of field.

On the other hand, as can be seen with reference to FIG. 6, by applying the optical element 12, the value of the modulation transfer function (MTF) at the focusing position is lower than that before the application of the optical element 12. Therefore, in the medical image processing system 1 according to the present embodiment, as illustrated in FIG. 5, by executing restoration processing (image processing) on an image captured by the camera head 13, the image is restored with respect to the deterioration (so-called blur) in the image of the subject image that is caused according to the decrease in the modulation transfer function (MTF). For example, in FIG. 5, an image indicated by a reference numeral v25 illustrates an example of a subject image, on which the restoration processing has been executed, in a case where the restoration processing is executed on a subject image v23. Note that the restoration processing (for example, processing for adjusting blur amount) includes, for example, processing called deconvolution. Of course, as long as the processing can restore the deterioration in the image, the restoration processing applied to the image of the subject image is not necessarily limited to only the deconvolution.

Under the above control, for example, the depth of field is expanded, and the image in which the observation target is more clearly presented (that is, sharper image) can be obtained.

The features of the optical element 12 which is inserted between the lens barrel 11 and the camera head 13 in the endoscope 10 according to the present embodiment have been described in detail above with reference to FIGS. 2 to 6.

3. Study on EDOF Technology Using Birefringent Mask

Subsequently, a technical problem in a case where the EDOF technology using the birefringent mask is applied as in the medical image processing system according to the present embodiment will be described.

In a case where the depth of field is expanded by a combination of the birefringent mask and the image processing (restoration processing), content of processing executed as the image processing is designed as assuming that optical characteristics of the birefringent mask and other optical systems are known.

Here, as described above, in the EDOF technology using the birefringent mask, for example, processing called deconvolution performed to remove a blur from the image captured via the optical system including the birefringent mask is applied as the image processing. In the deconvolution, by adaptively switching a filter coefficient of a filter to be applied according to the optical characteristics of the optical system including the birefringent mask, the blur caused by the insertion of the birefringent mask is removed.

Note that, as a deconvolution, filter for example, an inverse filter, a wiener filter, and the like can be exemplified. The inverse filter, for example, corresponds to a filter designed according to the optical characteristics (for example, modulation transfer function (MTF) and the like) of the optical system including the birefringent mask (for example, lens barrel of endoscope and the like). That is, for example, the inverse filter may be designed to have inverse characteristics to the modulation transfer function of the optical system.

Furthermore, spatial frequency characteristics WF of the wiener filter is expressed by the following calculation formula indicated as (Formula 1) below.

[Expression 1]

$$WF(u, v) = \frac{H^*(u, v)}{|H(u, v)|^2 + \frac{S_n(u, v)}{S_f(u, v)}} \quad \text{(Formula 1)}$$

In the above (Formula 1), u and v respectively express spatial frequencies to the x direction and the y direction in a case where directions that are parallel to an image plane and orthogonal to each other are the x direction and the y direction. Furthermore, H (u, v) represents an Optical Transfer Function (OTF). Note that H*(u, v) represents a complex conjugation of H (u, v). Furthermore, $S_f$ (u, v) and $S_n$ (u, v) respectively represent power spectra of an original image and noise.

On the other hand, each time when a medical device such as a camera head and a lens barrel of an endoscope (for example, rigid scope and flexible scope) that is used in a medical field such as surgery is used, autoclave (high-pressure steam) sterilization processing is executed on the medical device. Therefore, for example, there is a case where the optical characteristics of the optical system of the endoscope (that is, rigid scope and flexible scope), particularly, the optical characteristics of the birefringent mask gradually change by repeatedly executing the autoclave sterilization processing on the endoscope. Under such a situation, there is a case where the optical characteristics of the birefringent mask (that is, optical characteristics after change) are different from optical characteristics assumed by image signal processing and the difference affects image quality of an output image.

Specifically, as the optical characteristics of the birefringent mask, a parameter indicating a phase difference of light called retardation can be exemplified. The retardation is expressed by a product Δnd of a refractive index difference Δn (=ne−no) and a thickness d of a birefringent material. By applying so-called autoclave processing (high-pressure steam processing) such as the autoclave sterilization processing to the birefringent mask, it may be estimated that characteristics of the refractive index difference Δn of the birefringent mask change (that is, refractive index difference Δn decreases). By decreasing the value of the refractive index difference Δn, for example, an effect on the expansion of the depth of field is reduced.

On the other hand, even though the retardation of the birefringent mask is changed, if the image processing (restoration processing) similar to that before the change in the retardation is applied to the image captured by using the birefringent mask, there is a high possibility that the image quality of the output image becomes so-called overemphasis. Therefore, by adaptively switching the content of the image processing according to the change in the retardation of the birefringent mask, there is a case where it is desirable that an image having more preferred image quality can be output.

The optical characteristics (retardation) of the birefringent mask can be measured with the birefringent mask alone. However, there is a case where the birefringent mask is incorporated as a part of the optical system of the endoscope (for example, rigid scope), the optical system of the camera head, and the like. In such a case, it is difficult to measure the optical characteristics of the birefringent mask alone.

In consideration of the above situation, the present disclosure proposes a technology that can realize control of expansion of the depth of field by using the birefringent mask in a more preferred aspect. Specifically, the present disclosure proposes an example of a technology that can output an image in a more preferred aspect (for example, output with more preferable image quality) even under a situation in which the optical characteristics of the birefringent mask are changed by repeatedly executing the autoclave sterilization processing.

4. Technical Features

Technical features of a medical image processing system according to one embodiment of the present disclosure will be described below.

<4.1. Summary>

As described above, in a medical observation device, there is a case where the birefringent mask is incorporated as a part of the optical system such as the lens barrel or the camera head of the endoscope. In such a case, it is difficult to measure the optical characteristics of the birefringent mask alone later (that is, measure after incorporation). Therefore, under such a situation, for example, in a case where the optical characteristics (retardation) of the birefringent mask change by repeatedly executing the autoclave sterilization processing on a device in which the birefringent mask is incorporated, it is difficult to directly measure the change in the optical characteristics.

Therefore, the medical image processing system according to the present embodiment estimates the change in the optical characteristics (for example, retardation) of the birefringent mask according to the application situation of the autoclave sterilization processing and controls the image processing (image signal processing) to be applied to the image according to the estimation result.

As a specific example, according to application situations such as the number of times of application and an application time (integration time) of the autoclave processing on a device such as a lens barrel or a camera head of an endoscope (hereinafter, referred to as "target device"), the medical image processing system indirectly estimates a change in optical characteristics of a birefringent mask provided (incorporated) in the target device. Then, the medical image processing system controls the image processing (restoration processing) applied to an image captured by using the target device according to the estimation result regarding the change in the optical characteristics. As a specific example, the medical image processing system selectively switches a filter (for example, deconvolution filter) to be applied to the captured image according to the estimation result regarding the change in the optical characteristics.

Note that the application situation of the autoclave processing on each target device may be managed by, for example, the medical image processing system or may be managed by other system (for example, in-hospital system and the like) different from the medical image processing system. Furthermore, the application situation of the autoclave processing for each target device can be individually managed for each target device, for example, by identifying each target device on the basis of identification information (serial ID and the like) associated with the device.

Furthermore, as another example, by estimating the application situation of the autoclave processing on the target device according to the use time of the target device, the change in the optical characteristics of the birefringent mask provided in the target device may be estimated.

Furthermore, by estimating the application situation of the autoclave processing on the target device according to a detection result of a change in a temperature around the target device by a temperature sensor and the like, the change in the optical characteristics of the birefringent mask provided in the target device may be estimated. Specifically, in a case where the temperature sensor provided in a housing of a device such as a lens barrel or a camera head of the endoscope detects a temperature equal to or higher than a threshold, it is sufficient that it is recognized that the autoclave processing is applied to the target device and the number of times of application and the application time of the autoclave processing are counted.

Figure 7:
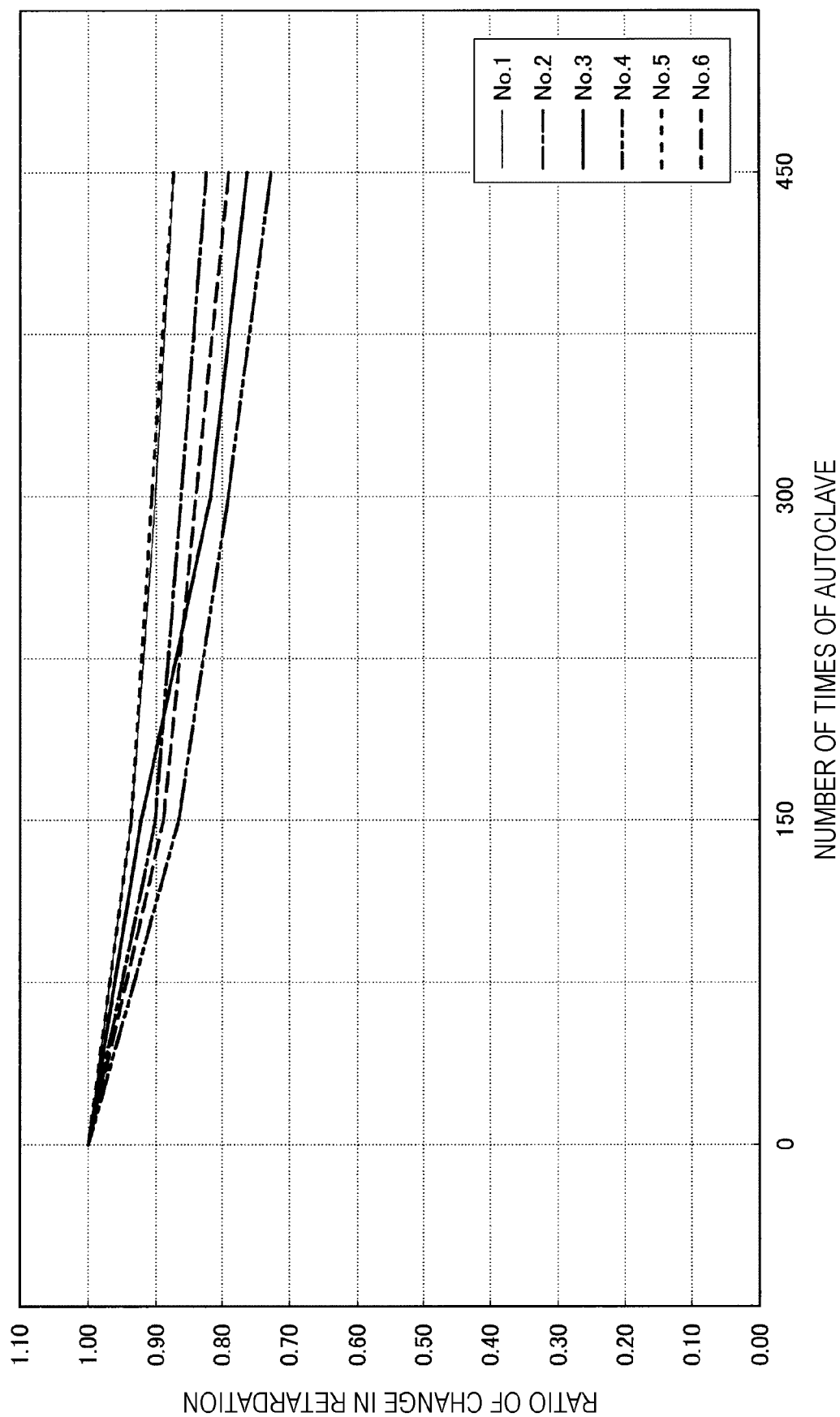
FIG. 7 is an explanatory diagram for explaining an example of a simulation result regarding a change in a retardation according to an application situation of autoclave processing.

Note that the change in the optical characteristics of the optical system of the target device (particularly, retardation of birefringent mask) according to the application situation of the autoclave processing on each target device such as the lens barrel or the camera head of the endoscope can be measured by experiments, simulations, and the like in advance. For example, FIG. 7 is an explanatory diagram for explaining an example of a simulation result regarding the change in the retardation according to the application situation of the autoclave processing. In FIG. 7, the horizontal axis indicates the number of times of the autoclave processing applied to the target device. Furthermore, the vertical axis indicates the change in the retardation of the target device by a ratio in a case where it is assumed that the retardation in the initial state (for example, at the time of shipment) be one. Note that, in the example illustrated in FIG. 7, regarding each of six types of devices indicated by "No. 1" to "No. 6", an example of a simulation result regarding the change in the retardation is illustrated.

As can be understood with reference to FIG. 7, as the number of times of application of the autoclave processing on the target device is increased, the retardation of the target device tends to decrease. That is, by individually managing the application situation (for example, the number of times of application and application time) of the autoclave processing for each target device from the example illustrated in FIG. 7, it can be found that it is possible to estimate the change in the retardation of the target device (that is, decrease in retardation). Therefore, by controlling the image processing such as deconvolution to be applied to the image acquired (captured) by using the target device according to the estimation result of the change in the retardation of the target device, it is possible to output an image in a more preferred aspect (for example, image with more preferred image quality).

With the above configuration, even under a situation in which the optical characteristics (retardation) of the birefringent mask incorporated in the endoscope and the like changes later by the autoclave processing and the like, it is possible to indirectly estimate the change in the optical characteristics and apply more preferred image processing on the captured image. Note that, hereinafter, the medical image processing system according to the present embodiment will be described in more detail.

<4.2. Functional Configuration>

Subsequently, an example of a functional configuration of the medical image processing system according to the present embodiment will be described as particularly focusing on a part regarding the EDOF technology using the birefringent mask. For example, FIG. 8 is a functional block diagram illustrating an example of a functional configuration of the medical image processing system according to the present embodiment.

Figure 8:
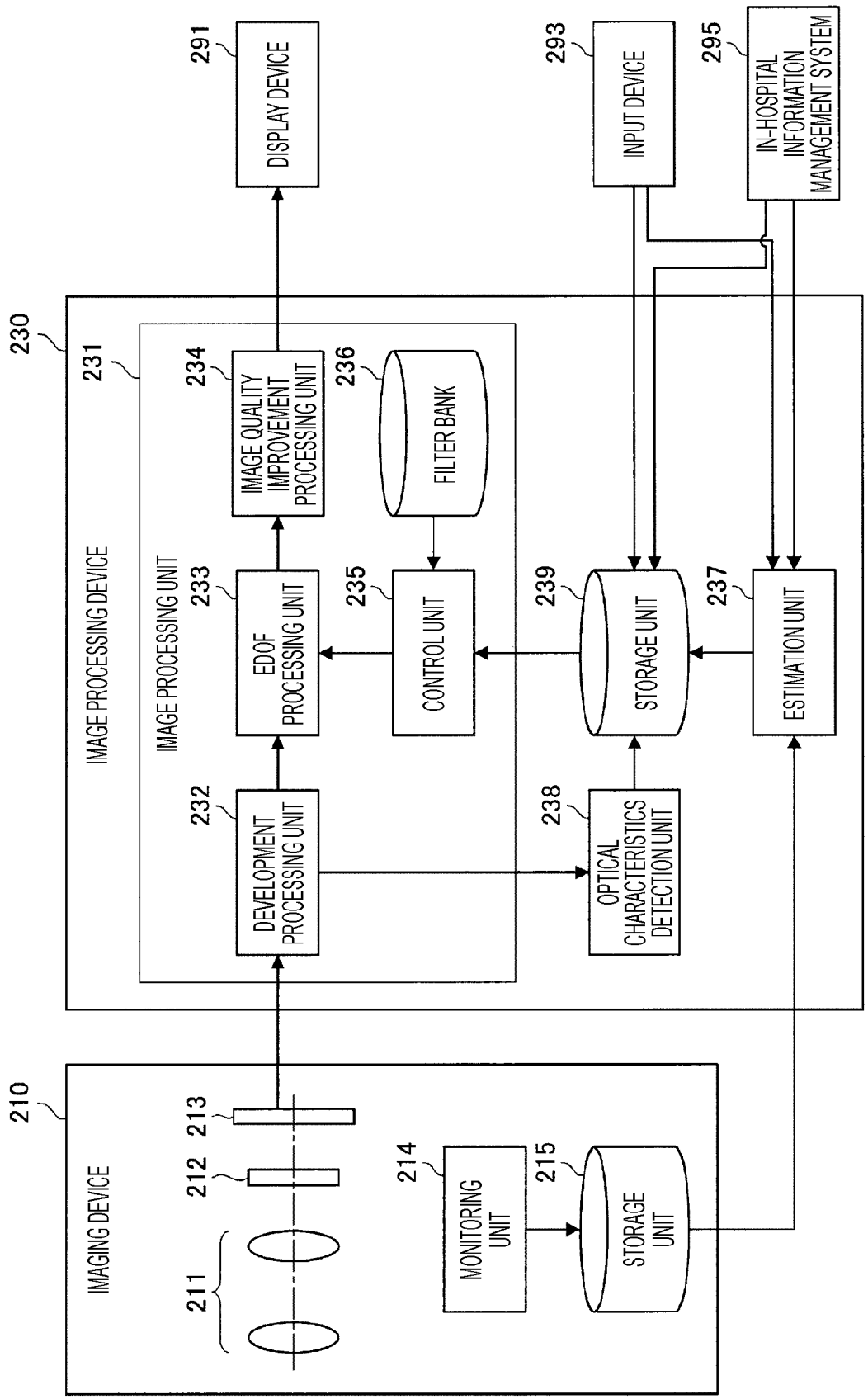
FIG. 8 is a functional block diagram illustrating an example of a functional configuration of a medical image processing system according to the embodiment.

As illustrated in FIG. 8, a medical image processing system 200 according to the present embodiment includes an imaging device 210, an image processing device 230, and a display device 291. Furthermore, the medical image processing system 200 may include an input device 293. Furthermore, the medical image processing system 200 may be connected to another system such as an in-hospital information management system 295 via a predetermined network.

The display device 291 corresponds to the display device 53 illustrated in FIG. 1 and displays information presented to the user (for example, image and the like) as display information. As a specific example, an image obtained by executing image processing (for example, corrected image) by the image processing device 230 on an image captured by the imaging device 210 is presented to the user via the display device 291.

The input device 293 corresponds to an input interface used by the user to input various information to each device included in the medical image processing system 200. The input device 293 receives an operation input of the user and inputs information according to the operation input to a predetermined device (for example, image processing device 230). With this operation, the device can recognize an instruction from the user and acquire information on the basis of the user input.

The in-hospital information management system 295 is a system for managing various information. For example, the in-hospital information management system 295 manages information such as a usage situation of the imaging device 210 or an application situation of the autoclave processing (for example, autoclave sterilization processing) on the imaging device 210. The in-hospital information management system 295 may be configured to be accessible via a predetermined network and may output information managed by the in-hospital information management system 295 to the other device in response to a request from the device (for example, image processing device 230) via the network. With such a configuration, the other device can acquire various information managed by the in-hospital information management system 295 by accessing the in-hospital information management system 295.

The imaging device 210 corresponds to the medical observation device (in other words, medical imaging device) that images an image of a patient and outputs the image to a predetermined output destination. As a specific example, the imaging device 210 corresponds to the endoscope 10 (that is, lens barrel 11 and camera head 13) illustrated in FIGS. 1 and 3. Note that, in this description, a case where the imaging device 210 is configured as an endoscope will be described as an example.

As illustrated in FIG. 8, the imaging device 210 includes an optical system 211 such as an objective lens, a birefringent mask 212, and an imaging element 213. The optical system 211 schematically indicates the lens barrel of the endoscope. Furthermore, the imaging element 213 schematically indicates an imaging element provided in the camera head. Furthermore, the birefringent mask 212 schematically indicates any one of birefringent masks 12a to 12c described with reference to FIG. 3. Note that a part including the optical system 211 and the birefringent mask 212 (that is, part corresponding to rigid scope, flexible scope, and the like) corresponds to an example of an "endoscope portion".

Furthermore, the imaging device 210 may include a monitoring unit 214 and a storage unit 215. The monitoring unit 214 monitors various states of the imaging device 210 and makes the storage unit 215 store information according to the monitoring. The storage unit 215 temporarily or permanently stores various information.

As a specific example, the monitoring unit 214 may include a detection unit that detects an ambient temperature such as a temperature sensor. In this case, the monitoring unit 214 may monitor temperatures (in other words, temperature change) around the optical system 211, the birefringent mask 212, and the imaging element 213 detected by the detection unit and make the storage unit 215 store information according to the result of the monitoring. With such a configuration, for example, if the autoclave processing is applied to the imaging device 213, the detection unit detects the temperature change caused by the autoclave processing, and the storage unit 215 stores the detection result of the temperature change.

Furthermore, as another example, the monitoring unit 214 may include a clocking unit, monitor a use time (for example, imaging time, driving time, and the like) of the imaging device 210 by using the clocking unit, and make the storage unit 215 store information according to the result of monitoring (for example, information indicating use time).

Note that various information stored in the storage unit 215 may be, for example, output to other device (for example, image processing device 230) via a predetermined interface.

The image processing device 230 generates an output image by executing various image processing such as development processing on the image signal output from the imaging device 210 according to the imaging result by the imaging device 210 and makes the display device 291 display the output image. Note that the image processing device 230 may be configured as, for example, the CCU 51 illustrated in FIG. 1. That is, the image processing device 230 corresponds to an example of the "medical image processing apparatus".

Specifically, as illustrated in FIG. 8, the image processing device 230 includes an image processing unit 231, an estimation unit 237, and a storage unit 239. Furthermore, the image processing device 230 may include an optical characteristics detection unit 238. Furthermore, the image processing unit 231 includes, for example, a development processing unit 232, an EDOF processing unit 233, an image quality improvement processing unit 234, and a control unit 235. Furthermore, the image processing unit 231 may include a filter bank 236.

The estimation unit 237 acquires various information from the imaging device 210 and estimates the application situation of the autoclave processing on the imaging device 210 according to the acquired information.

As a specific example, the estimation unit 237 may estimate the number of times of autoclave processing applied to the imaging device 210 according to the monitoring result of the temperatures around the optical system 211, the birefringent mask 212, and the imaging element 213. Furthermore, the estimation unit 237 may estimate the number of times of autoclave processing applied to the imaging device 210 according to the monitoring result of the use time of the imaging device 210. Furthermore, by acquiring the identification information from the imaging device 210 and recognizing the imaging device 210, the estimation unit 237 may individually estimate the application situation (for example, the number of times) of the autoclave processing applied to the imaging device 210 for each imaging device 210. With such a configuration, even under a situation in which any one of the plurality of imaging devices 210 is selectively used, it is possible to individually estimate the application situation of the autoclave processing for each imaging device 210 which is used.

Furthermore, the estimation unit 237 may estimate an accumulated time in which the autoclave processing is applied to the imaging device 210. For example, the estimation unit 237 may estimate the accumulated time in which the autoclave processing is applied by multiplying the estimation result of the number of times of application of the autoclave processing by the application time of the autoclave processing each time which has been set in advance. Furthermore, the application situation (for example, accumulated time) of the autoclave processing may be estimated by the estimation unit 237 according to the time of the each autoclave processing that is applied to the imaging device 210 each time.

Furthermore, as the other example, the estimation unit 237 may acquire various information regarding the imaging device 210 managed by the in-hospital information management system 295 from the in-hospital information management system 295. In this case, the estimation unit 237 may estimate the application situation of the autoclave processing on the imaging device 210 on the basis of the information acquired from the in-hospital information management system 295. As the information acquired from the in-hospital information management system 295, for example, information regarding an accumulated use time of the imaging device 210, information regarding the number of times of application of the autoclave processing on the imaging device 210, the information regarding the accumulated time in which the autoclave processing is applied to the imaging device 210, and the like can be exemplified. Note that, the information above is merely an example, and the information is not necessarily limited to only the example described above as long as the information is information from which the application situation of the autoclave processing on the imaging device 210 can be recognized or estimated by the estimation unit 237.

Furthermore, as the other example, the estimation unit 237 may acquire various information regarding the imaging device 210 on the basis of a user input via an input interface such as the input device 293. In this case, the estimation unit 237 may estimate the application situation of the autoclave processing on the imaging device 210 on the basis of the information that is acquired on the basis of the user input. Note that as long as the estimation unit 237 can recognize or estimate the application situation of the autoclave processing on the imaging device 210, the information acquired as the user input is not particularly limited.

Then, the estimation unit 237 may make the storage unit 239 store information according to the estimation result of the application situation of the autoclave processing on the imaging device 210. Furthermore, as the other example, the estimation unit 237 may directly output the information according to the estimation result of the application situation of the autoclave processing on the imaging device 210 to the control unit 235 to be described later.

The optical characteristics detection unit 238 detects the change in the optical characteristics of the series of optical systems included in the imaging device 210 (for example, optical system 211 and birefringent mask 212) by analyzing an image generated on the basis of the image signal output from the imaging device 210 by the development processing unit 232 to be described later. This makes it possible to indirectly estimate the change in the optical characteristics (for example, retardation) of the birefringent mask 212. Note that the optical characteristics detection unit 238 may make the storage unit 239 store the information according to the detection result of the change in the optical characteristics. Furthermore, as the other example, the optical characteristics detection unit 238 may directly output the information according to the detection result of the change in the optical characteristics to the control unit 235 to be described later.

Note that, at the time of an operation such as a so-called calibration and the like (for example, system maintenance work), the optical characteristics detection unit 238 may detect the change in the optical characteristics of the series of optical systems included in the imaging device 210 by using a known calibration chart (for example, image of pattern and edge including white and black and the like). In this case, the optical characteristics detection unit 238 may detect the change in the optical characteristics of the series of optical systems included in the imaging device 210 on the basis of the image features such as the pattern or the edge in the image of the calibration chart imaged by the imaging device 210.

The storage unit 239 temporarily or permanently stores various information. For example, as described above, the storage unit 239 may store the information according to the estimation result of the application situation of the autoclave processing on the imaging device 210, the information according to the detection result of the change in the optical characteristics of the series of optical systems included in the imaging device 210, and the like. Furthermore, the storage unit 239 may store information input by the user via a predetermined input interface such as the input device 293 or the like, information transmitted from the in-hospital information management system 295 and the like (for example, information managed by in-hospital information management system 295), and the like. As a specific example, the information regarding the application situation of the autoclave processing on the imaging device 210 may be acquired on the basis of the user input via the input device 293 and stored in the storage unit 239. Furthermore, the information regarding the application situation of the autoclave processing on the imaging device 210 may be transmitted from the in-hospital information management system 295, and the information may be stored in the storage unit 239.

The development processing unit 232 generates an image on the basis of the image signal (that is, image based on imaging result by imaging device 210) by executing so-called development processing on the image signal output from the imaging device 210. The development processing unit 232 outputs the generated image to the EDOF processing unit 233 positioned at the subsequent stage.

The EDOF processing unit 233 executes the restoration processing (for example, filter processing) such as the deconvolution on the image output from the development processing unit 232 positioned at the preceding stage (that is, image based on image signal from imaging device 210) so as to restore a blur of the image caused in accordance with the application of the birefringent mask 212. With this operation, the depth of field is further expanded, and the corrected image of which the blur is restored is generated. Note that the restoration processing by the EDOF processing unit 233 is controlled by the control unit 235 to be described later. As a specific example, a filter applied to the input image by the EDOF processing unit 233 may be switched by the control unit 235. Furthermore, as the other example, a coefficient of the filter processing applied on the input image by the EDOF processing unit 233 may be controlled by the control unit 235. Then, the EDOF processing unit 233 outputs the generated corrected image (that is, image of which blur is corrected) to the image quality improvement processing unit 234 positioned at the subsequent stage.

The image quality improvement processing unit 234 executes various image processing on the image (that is, corrected image) output from the EDOF processing unit 233 positioned at the preceding stage and outputs the image, on which the image processing has been executed, to a predetermined output destination. As a specific example, the image quality improvement processing unit 234 may display the image on the display device 291 by outputting the image, on which the image processing has been executed, to the display device 291 connected to the image processing device 230 via a predetermined transmission path. Note that the type of the image processing applied to the input image by the image quality improvement processing unit 234 may be appropriately determined according to the use of the image output from the image quality improvement processing unit 234. Furthermore, the type of the image processing applied to the input image by the image quality improvement processing unit 234 may be selectively switched according to an instruction from a user via a predetermined input interface.

The control unit 235 controls the operation of the EDOF processing unit 233, that is, the restoration processing (that is, image processing) such as the deconvolution on the input image by the EDOF processing unit 233 under a predetermined condition. For example, the control unit 235 may control the operation of the EDOF processing unit 233 according to the application situation of the autoclave processing on the imaging device 210. At this time, the control unit 235 may selectively switch the filter applied to the input image by the EDOF processing unit 233.

Specifically, as the retardation of the birefringent mask 212 is deteriorated by the application of the autoclave processing, for example, the effect of the expansion of the depth of field is reduced, and a deterioration amount (that is, amount of blur) of the input image is reduced. Therefore, for example, the control unit 235 may suppress an application amount of the restoration processing on the image according to the reduction in the amount of blur. As a result, it is possible to prevent a case where the image quality of the output image becomes so-called overemphasis and perform control to output an image with more preferred image quality.

Note that information regarding the filter to be applied may be stored, for example, in a predetermined storage region. For example, the filter bank 236 illustrated in FIG. 8 schematically illustrates a storage region that holds information regarding various filters which are applied to the input image by the EDOF processing unit 233. Note that a component corresponding to the filter bank 236 may be provided outside the image processing unit 231 or may be provided outside the image processing device 230.

Furthermore, as the other example, the control unit 235 may perform control so that correction processing (for example, filter) for expanding the depth of field to compensate the reduction is applied to the input image according to the reduction in the effect of the expansion of the depth of field by the birefringent mask 212. In other words, the control unit 235 may perform control so that the correction processing for expanding the depth of field is applied to the input image according to the application situation (for example, integration time) of the autoclave processing. Furthermore, at this time, the control unit 235 may perform control the application amount of the correction processing according to the application situation of the autoclave processing. In this case, for example, the control unit 235 may perform control so that the application amount of the correction processing regarding the expansion of the depth of field is more increased as the integration time of the autoclave processing executed on the imaging device 210 increases.

Note that the correction processing for expanding the depth of field of the input image described above may be realized by applying, for example, so-called machine learning. Specifically, it is sufficient that machine learning (for example, machine learning using multilayer neural network) be performed by using an image to which the autoclave processing is not applied (for example, image of which depth of field is expanded by EDOF technology) as learning data and the correction processing be executed on the basis of a result of the machine learning. That is, in a case where the integration time of the autoclave processing executed on the imaging device 210 exceeds a threshold, the control unit 235 is only required to perform control so that the correction processing for expanding the depth of field is applied to the input image by using the result of the machine learning.

Furthermore, as the other example, the correction processing for expanding the depth of field of the input image described above may be realized by adding processing for synthesizing a plurality of images having different focal lengths.

Note that the control unit 235 may use, for example, the information stored in the storage unit 239 according to the estimation result by the estimation unit 237 as the information regarding the application situation of the autoclave processing on the imaging device 210. Furthermore, the control unit 235 may directly acquire the estimation result by the estimation unit 237 from the estimation unit 237.

Furthermore, an acquisition source of the information regarding the application situation of the autoclave processing on the imaging device 210 is not necessarily limited to only the storage unit 239 and the estimation unit 237. As a specific example, the information may be acquired on the basis of the user input via the input interface such as the input device 293. Furthermore, as the other example, the information may be acquired from the in-hospital information management system 295. Note that a part, which acquires the information, of the control unit 235 corresponds to an example of an "acquisition unit".

Furthermore, the control unit 235 may control the operation of the EDOF processing unit 233 according to the detection result of the change in the optical characteristics of the series of optical systems included in the imaging device 210. As a specific example, the control unit 235 may control the filter of which an instruction on the application to the input image is given to the EDOF processing unit 233 according to the application situation of the autoclave processing on the imaging device 210 depending on the detection result of the change in the optical characteristics of the series of optical systems. Note that this operation will be separately described in detail later as a modification. Furthermore, the control unit 235 may directly specify the filter applied to the input image by the EDOF processing unit 233 according to the detection result of the change in the optical characteristics of the series of optical systems. For example, the control unit 235 may estimate the change in the optical characteristics (for example, retardation) of the birefringent mask 212 included in the series of optical systems according to the detection result and determine the filter of which an instruction on the application to the input image is given to the EDOF processing unit 233 according to a result of the estimation.

Note that the functional configuration of the medical image processing system 200 described above is merely an example. As long as each function can be realized, the functional configuration of the medical image processing system 200 is not necessarily limited to the example illustrated in FIG. 8. As a specific example, at least two or more devices of the imaging device 210, the image processing device 230, and the display device 291, and the input device 293 may be integrally formed. Furthermore, some components of the components of the image processing device 230 may be provided outside (for example, server and the like) of the image processing device 230. Furthermore, each function of the image processing device 230 may be realized by operating the plurality of devices in cooperation.

The example of the functional configuration of the medical image processing system according to the present embodiment has been described above as particularly focusing on a part regarding the EDOF technology using the birefringent mask with reference to FIG. 8.

<4.3. Processing>

Figure 9:
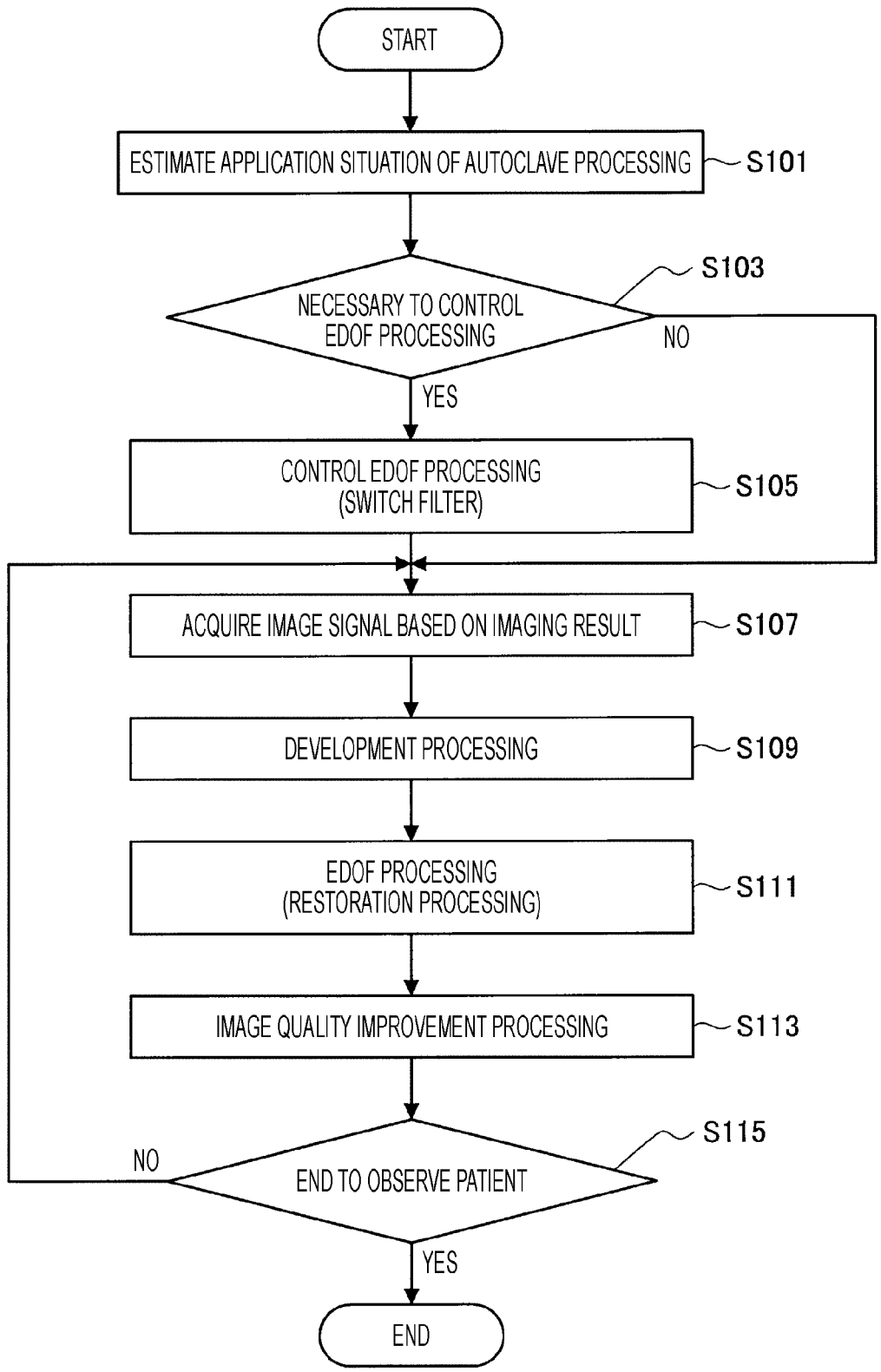
FIG. 9 is a flowchart illustrating an example of a flow of a series of processing of the medical image processing system according to the embodiment.

Subsequently, an example of a flow of a series of processing of the medical image processing system according to the present embodiment will be described as particularly focusing on the operation of the image processing device 230 illustrated in FIG. 8. For example, FIG. 9 is a flowchart illustrating the example of the flow of the series of processing of the medical image processing system according to the present embodiment. Specifically, FIG. 9 illustrates an example in a case where the image processing device 230 estimates the application situation of the autoclave sterilization processing on the imaging device 210 and controls the restoration processing in the EDOF technology using the birefringent mask according to a result of the estimation in the medical image processing system 200 illustrated in FIG. 8.

First, the image processing device 230 (estimation unit 237) acquires various information (for example, information regarding use time of imaging device 210 and the like) from the imaging device 210 and estimates the application situation of the autoclave sterilization processing on the imaging device 210 according to the acquired information (S101). Then, the image processing device 230 (control unit 235) determines whether or not it is necessary to control of the EDOF processing applied to an input image, that is, an image based on the image signal from the imaging device 210 according to a result of the estimation (S103).

In a case where the image processing device 230 (control unit 235) determines that it is necessary to control the EDOF processing (that is, restoration processing such as deconvolution) applied to the input image (YES in S103), the image processing device 230 controls the EDOF processing according to the estimation result of the application situation of the autoclave sterilization processing on the imaging device 210. As a specific example, the image processing device 230 may selectively switch a deconvolution filter applied to the input image according to the application situation of the autoclave sterilization processing on the imaging device 210 (S105). Note that, in a case where the image processing device 230 determines that it is not necessary to control the EDOF processing (NO in S103), the image processing device 230 shifts to next processing without executing processing regarding the control of the EDOF processing.

Next, the image processing device 230 (development processing unit 232) acquires an image signal output on the basis of the imaging result from the imaging device 210 (S107) and generates an image based on the acquired image signal (that is, image based on imaging result by imaging device 210) by executing the development processing on the image signal (S109).

The image processing device 230 (EDOF processing unit 233) executes the restoration processing such as the deconvolution on the image generated on the basis of the development processing so as to restore a blur of the image caused according to the application of the birefringent mask 212 (S111). With this operation, the depth of field is further expanded, and the corrected image of which the blur is restored is generated. Note that, as described above, the restoration processing is controlled according to the application situation of the autoclave sterilization processing on the imaging device 210. Furthermore, the image processing device 230 (image quality improvement processing unit 234) executes various image processing (for example, image processing for improving image quality) on the corrected image and outputs the image-processed image to a predetermined output destination (S113).

As described above, the image processing device 230 sequentially executes processing indicated by reference numerals S107 to S113 until an instruction on an end of observation of a patient is given (NO in S115). Then, when the instruction on the end of the observation of the patient is given (YES in S115), the image processing device 230 ends the series of processing described above.

The example of the flow of the series of processing of the medical image processing system according to the present embodiment has been described above with reference to FIG. 9 as particularly focusing on the operation of the image processing device 230 illustrated in FIG. 8.

<4.4. Modification>

Subsequently, a modification of the medical image processing system according to the present embodiment will be described.

(First Modification: Dynamic Filter Generation)

First, as a first modification, an example of a case will be described where the image processing device 230 dynamically generates a part of a filter (that is, deconvolution filter) applied to the input image according to the application situation of the autoclave processing on the imaging device 210 from another filter. Note that, the description will be made as focusing on a case where the image processing device 230 determines a filter applied to the input image according to the number of times of application of the autoclave processing on the imaging device 210.

Figure 10:
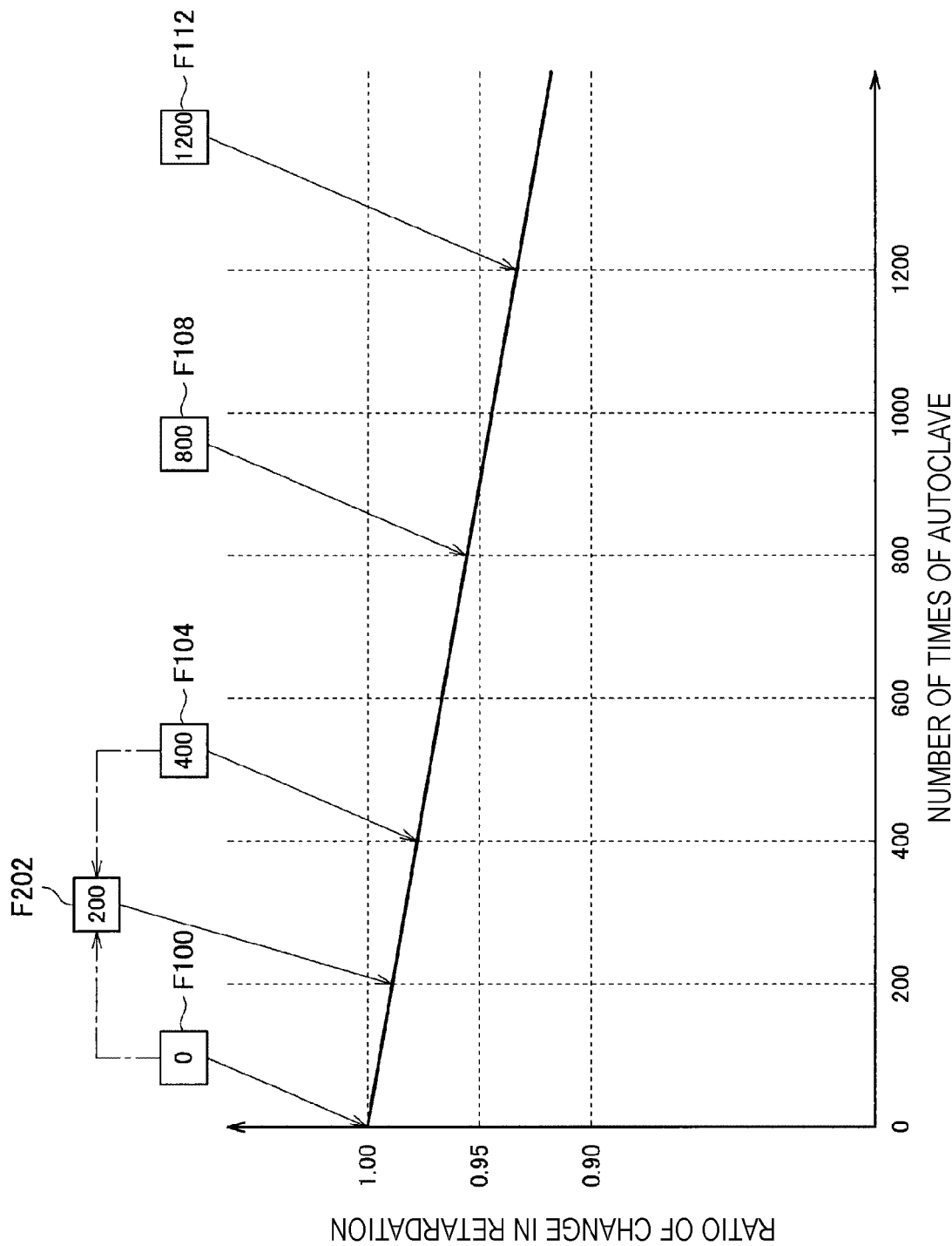
FIG. 10 is an explanatory diagram for explaining an outline of a medical image processing system according to a first modification.

For example, FIG. 10 is an explanatory diagram for explaining an outline of a medical image processing system according to the first modification and illustrates an example of a change in optical characteristics of the birefringent mask 212 provided in the imaging device 210 according to the number of times of application of the autoclave processing on the imaging device 210. In FIG. 10, the horizontal axis indicates the number of times of autoclave processing applied to the target device. Furthermore, the vertical axis indicates the change in the retardation of the target device by a ratio in a case where it is assumed that the retardation in the initial state (for example, at the time of shipment) be one.

In the example illustrated in FIG. 10, filters F100, F104, F108, and F112 are previously generated as filters according to the number of times of application of the autoclave processing on the imaging device 210 and are held in a predetermined storage region (for example, filter bank 236 illustrated in FIG. 8). Note that the filter F100 is adjusted to execute the restoration processing on the input image in accordance with the optical characteristics of the birefringent mask in a case where the number of times of application of the autoclave processing on the imaging device 210 is zero. That is, in a case where the number of times of application of the autoclave processing on the imaging device 210 is zero, the image processing device 230 executes the restoration processing based on the filter F100 on the input image (that is, image based on imaging result by imaging device 210). Similarly, the filters F104, F108, and F112 respectively correspond to cases where the numbers of times of application of the autoclave processing on the imaging device 210 are 400 times, 800 times, and 1200 times.

That is, in the example illustrated in FIG. 10, filters are not generated in advance for all the number of times of application of the autoclave processing, and filters discretely corresponding to each predetermined number of times (for example, every 400 times) are generated.

Based on such a configuration, in a case where the filter corresponding to the number of times of application of the autoclave processing is not generated, the image processing device 230 according to the first modification may dynamically generate the filter corresponding to the number of times of application by using at least any one of the generated filters.

As a specific example, in the example illustrated in FIG. 10, it is assumed that the number of times of application of the autoclave processing on the imaging device 210 be 200. In this case, the corresponding filter is not generated in advance. Therefore, the image processing device 230 may generate a filter F202 corresponding to a case of 200 times on the basis of the filter F100 corresponding to a case where the number of times of application of the autoclave processing is zero and the filter F104 corresponding to a case of 400 times. Specifically, the image processing device 230 may generate the filter F202 corresponding to a case where the number of times of application of the autoclave processing is 200 on the basis of linear interpolation using filter coefficients of the filters F100 and F104. This is similar to that in a case where the number of times is different. That is, a filter corresponding to a case where the number of times of application of the autoclave processing is 600 can be generated, for example, on the basis of linear interpolation using filter coefficients of the filters F104 and F106.

With the above configuration, in the medical image processing system according to the first modification, it is possible to limit the number of filters that are generated in advance according to the number of times of application of the autoclave processing. That is, it is possible to limit a capacity of the information regarding the filter held in the predetermined storage region.

Note that, in the above, it has been described an example in a case where the filter applied to the input image is controlled according to the number of times of application of the autoclave processing on the imaging device 210. However, processing regarding control of the filter by the image processing device 230 is not necessarily limited. That is, as long as the image processing device 230 can generate a filter corresponding to another application situation on the basis of the filter generated in advance according to a predetermined application situation, an aspect of the image processing device 230 is not particularly limited. As a specific example, the filter may be generated in correspondence with the accumulated time of the autoclave processing executed on the imaging device 210.

Furthermore, in the above, it has been described as focusing on a case where the filter processing is applied to the input image. However, a target of the control by the image processing device 230 is not necessarily limited to filter processing. That is, the image processing device 230 may generate image processing corresponding to the other application situation on the basis of the image processing on the input image that has been set in advance according to a predetermined application situation.

In the above, with reference to FIG. 10, as the first modification, an example has been described in a case where the image processing device 230 dynamically generates a part of the filters applied to the input image according to the application situation of the autoclave processing on the imaging device 210 from the other filter.

(Second Modification: Control Example of Restoration Processing)

Subsequently, as a second modification, an example of control of the restoration processing according to the application situation of the autoclave processing on the imaging device 210 will be described. Note that, the description will be made as focusing on a case where the image processing device 230 determines a filter applied to the input image according to the number of times of application of the autoclave processing on the imaging device 210.

As described above, in the medical image processing system according to the present embodiment, the image processing device 230 estimates the change in the optical characteristics (for example, retardation) of the birefringent mask 212 provided in the imaging device 210 according to the application situation (for example, the number of times of application) of the autoclave processing on the imaging device 210. On the other hand, depending on various error factors, an individual difference of the imaging device 210, and the like, there is a case where the change in the optical characteristics of the birefringent mask 212 estimated according to the application situation of the autoclave processing differs from an actual change in the optical characteristics of the birefringent mask 212.

In consideration of such a situation, in the medical image processing system according to the second modification, the image processing device 230 controls the filter processing applied to the input image according to the application situation of the autoclave processing on the imaging device 210 according to a predetermined condition.

Figure 11:
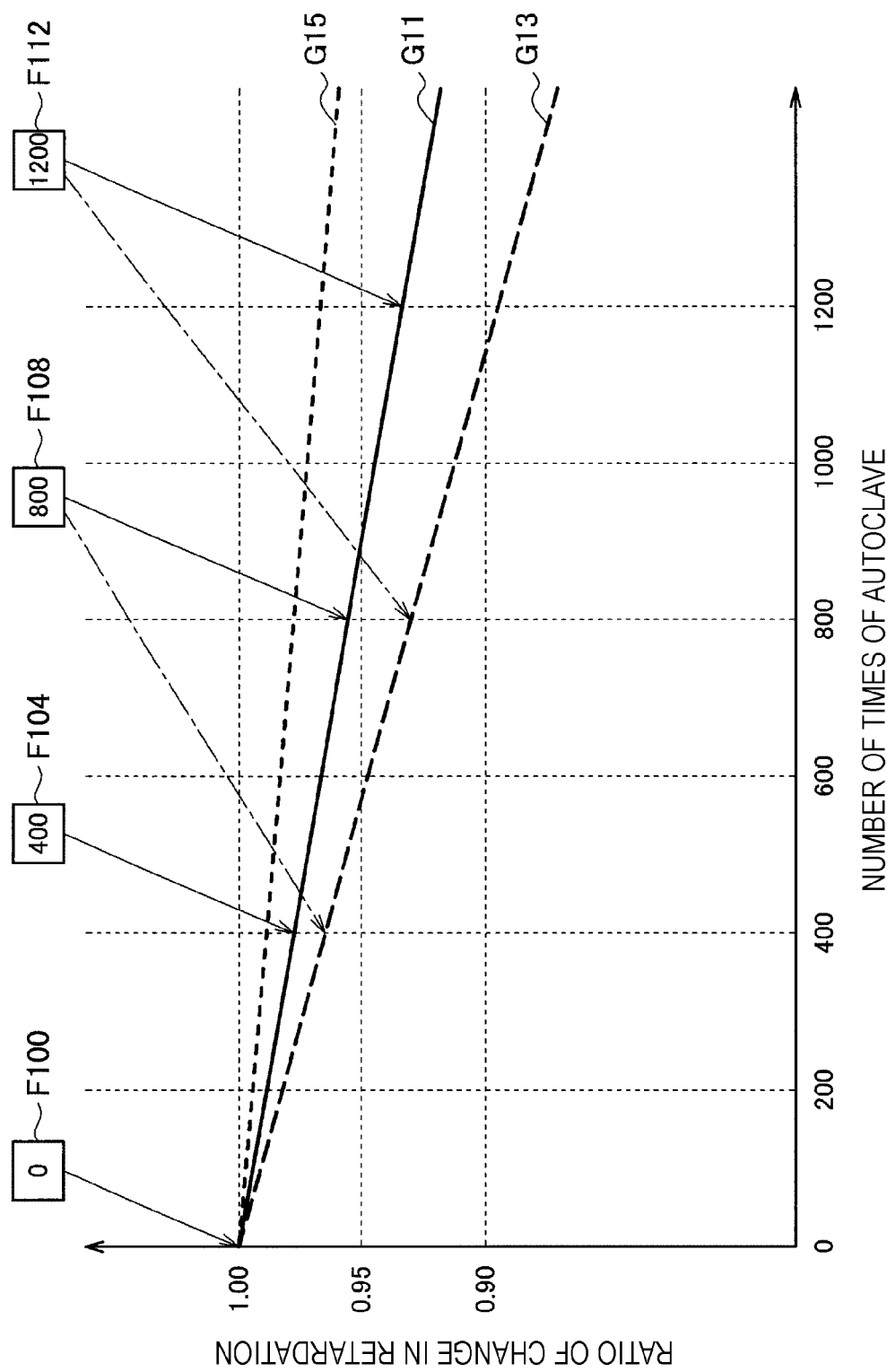
FIG. 11 is an explanatory diagram for explaining an outline of a medical image processing system according to a second modification.

For example, FIG. 11 is an explanatory diagram for explaining an outline of the medical image processing system according to the second modification and illustrates an example of a change in optical characteristics of the birefringent mask 212 provided in the imaging device 210 according to the number of times of application of the autoclave processing on the imaging device 210. Note that the horizontal axis and the vertical axis in FIG. 11 are respectively similar to those in the example illustrated in FIG. 10.

In FIG. 11, a graph indicated by a reference numeral G11 illustrates a case where the optical characteristics of the birefringent mask 212 change (deteriorate) as initially assumed according to the application situation of the autoclave processing on the imaging device 210. On the other hand, a graph indicated by a reference numeral G13 illustrates an example in a case where the optical characteristics of the birefringent mask 212 deteriorate more rapidly than initially assumed. Furthermore, a graph indicated by a reference numeral G15 illustrates an example in a case where the optical characteristics of the birefringent mask 212 deteriorate more slowly than initially assumed.

Specifically, a case indicated by the graph G13, if the optical characteristics of the birefringent mask 212 in a case where the number of times of application of the autoclave processing is 800 are as initially assumed (that is, case of graph G11), the deterioration is progressed to the optical characteristics in a case where the number of times of application of the autoclave processing is 1200. Under such a situation, even if the restoration processing (that is, filter) assuming a case where the number of times of application of the autoclave processing is 800 is applied to the input image, there is a case where a corrected image with image quality in a more preferred aspect is not generated. Similarly, in a case indicated by the graph G13, if the optical characteristics of the birefringent mask 212 are initially assumed in a case where the number of times of application of the autoclave processing is 400, the deterioration is progressed to the optical characteristics in a case where the number of times of application of the autoclave processing is 800. Even in this case, even if the restoration processing is applied as initially assumed, there is a case where a corrected image with image quality in a more preferred aspect is not generated.

Furthermore, in a case indicated by the graph G15, if the optical characteristics of the birefringent mask 212 are as initially assumed in a case where the number of times of application of the autoclave processing is 800, the deterioration is progressed only to the optical characteristics in a case where the number of times of application of the autoclave processing is 400. Under such a situation, even if the restoration processing (that is, filter) assuming a case where the number of times of application of the autoclave processing is 800 is applied to the input image, there is a case where a corrected image with image quality in a more preferred aspect is not generated.

In consideration of such a situation, the image processing device 230 according to the second modification can selectively switch the restoration processing (for example, filter) applied to the input image according to the application situation of the autoclave processing according to a predetermined condition.

As a specific example, the image processing device 230 may present the application result of the restoration processing on the input image to a user via the display device 291 and make the user select a filter to be applied as the restoration processing. In this case, the image processing device 230 may switch the restoration processing applied to the input image according to the application situation of the autoclave processing thereafter according to the selection result of the filter by the user. Specifically, according to the selection result of the filter by the user, the image processing device 230 may switch the selection of the filter, performed later, according to the application situation of the autoclave processing from selection based on the characteristics indicated in the graph G11 to selection based on the characteristics indicated in the graph G13 or G15.

Furthermore, the image processing device 230 may switch the restoration processing which is applied later to the input image according to the application situation of the autoclave processing on the basis of the detection result of the change in the optical characteristics of the series of optical systems included in the imaging device 210 obtained as a result of an operation such as calibration.

Furthermore, the image processing device 230 may analyze the image captured by the imaging device 210 and adaptively switch the restoration processing applied to the input image according to the application situation of the autoclave processing later on the basis of a result of the analysis. In this case, for example, the image processing device 230 may detect or estimate a degree of deterioration (in other words, amount of blur) of the image on the basis of the image analysis and adaptively switch the restoration processing applied to the image and an image input later in accordance with the result of the detection or the estimation.

As the second modification, the example of the control of the restoration processing according to the application situation of the autoclave processing on the imaging device 210 has been described above with reference to FIG. 11.

(Third Modification: Method of Presenting Filter to User)

Subsequently, as a third modification, as described above as the second modification, an example of a method of presenting a filter option to the user in a case where the user selects the filter applied as the restoration processing on the input image will be described. Note that, the description will be made as focusing on a case where the image processing device 230 determines a filter applied to the input image according to the number of times of application of the autoclave processing on the imaging device 210.

Figure 12:
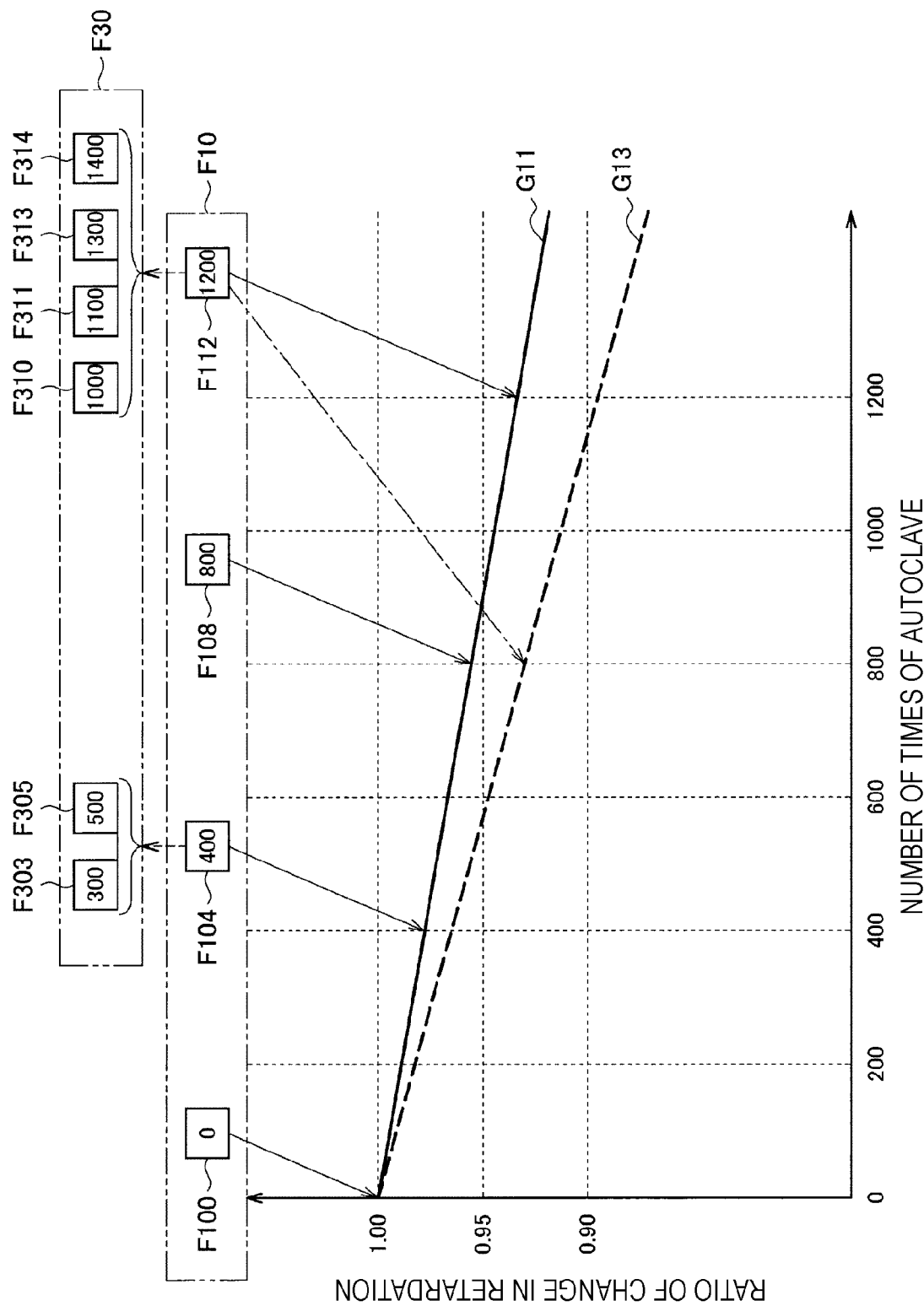
FIG. 12 is an explanatory diagram for explaining an outline of a medical image processing system according to a third modification.

The image processing device 230 according to the third modification controls the number of selectable candidates according to a situation when candidates of the selectable filter are presented to the user. For example, FIG. 12 is an explanatory diagram for explaining an outline of a medical image processing system according to the third modification and illustrates an example of a change in optical characteristics of the birefringent mask 212 provided in the imaging device 210 according to the number of times of application of the autoclave processing on the imaging device 210. Note that the horizontal axis and the vertical axis in FIG. 12 are respectively similar to those in the example illustrated in FIG. 10.

In FIG. 12, a graph indicated by a reference numeral G11 illustrates a case where the optical characteristics of the birefringent mask 212 change as initially assumed according to the application situation of the autoclave processing on the imaging device 210. On the other hand, a graph indicated by a reference numeral G13 illustrates an example in a case where the optical characteristics of the birefringent mask 212 deteriorate more rapidly than initially assumed. Furthermore, the filters F100, F104, F108, and F112 respectively indicate filters to which similar references are applied in the example illustrated in FIG. 10. That is, a series of filters indicated by a reference numeral F10 (filters F100, F104, F108, and F112) indicate filters scheduled to be applied to the input image in a case where the optical characteristics of the birefringent mask 212 change as initially assumed according to the application situation of the autoclave processing on the imaging device 210.

Furthermore, a series of filters indicated by a reference numeral F30 schematically illustrate options of filters that are presented to the user as the selectable candidates.

For example, filters F303 and F305 schematically illustrate filters assuming cases where the numbers of times of application of the autoclave processing are 300 and 500. In the example illustrated in FIG. 12, the image processing device 230 presents the filters F303 and F305 as candidates of selectable filters to the user in a case where the number of times of application of the autoclave processing is 400.

Furthermore, filters F310, F311, F313, and F314 schematically illustrate filters assuming cases where the numbers of times of application of the autoclave processing are 1000, 1100, 1300, and 1400. In the example illustrated in FIG. 12, the image processing device 230 presents the filters F310, F311, F313, and F314 as the candidates of the selectable filters to the user in a case where the number of times of application of the autoclave processing is 1200.

As described above, the image processing device 230 according to the third modification may control the number of candidates of the filters to be selectably presented to the user, for example, according to the number of times of application of the autoclave processing on the imaging device 210. Specifically, regarding the change in the optical characteristics of the birefringent mask 212, a difference from the initially predicted value tends to be smaller as the number of times of application of the autoclave processing is smaller, and the difference tends to be larger as the number of times of application is larger. Therefore, for example, in a case where the number of times of application of the autoclave processing is less than a threshold, the difference from the initially predicted value is small. Therefore, the image processing device 230 may limit the number of filters to be presented to the user as the selectable candidates. Furthermore, since the difference from the initially predicted value is larger as the number of times of application of the autoclave processing is larger, the image processing device 230 may perform control to increase the number of filters to be presented to the user as the selectable candidates.

Furthermore, the image processing device 230 may control the number of filters to be presented to the user as the selectable candidates according to the detection result of the change in the optical characteristics of the series of optical systems included in the imaging device 210 (for example, optical system 211 and birefringent mask 212). For example, in a case where a difference between the detection result of the change in the optical characteristics of the series of optical systems and the initially predicted value regarding the change in the optical characteristics is larger (for example, larger than threshold), the image processing device 230 may perform control to increase the number of filters to be presented to the user as the selectable candidates. As a more specific example, in a case where the deterioration in the optical characteristics (for example, retardation of birefringent mask 212) of the series of optical systems is progressed than the initial prediction, the image processing device 230 may perform control to increase the number of filters to be presented to the user as the selectable candidates.

Note that, in the above, the example in a case where the number of filters to be presented to the user as the selectable candidates is controlled according to the number of times of application of the autoclave processing on the imaging device 210 has been described. However, the present disclosure is not necessarily limited to the above aspect. That is, as long as the image processing device 230 can control the number of filters to be presented to the user as the selectable candidates according to the application situation of the autoclave processing on the imaging device 210, the aspect is not particularly limited. As a specific example, the image processing device 230 may control the number of filters to be presented to the user as the selectable candidates according to the accumulated time of the autoclave processing executed on the imaging device 210.

As the third modification, the example of the method of presenting the filter option to the user in a case where the user selects the filter applied to the input image as the restoration processing as described as the second modification has been described with reference to FIG. 12.

5. Hardware Configuration

Figure 13:
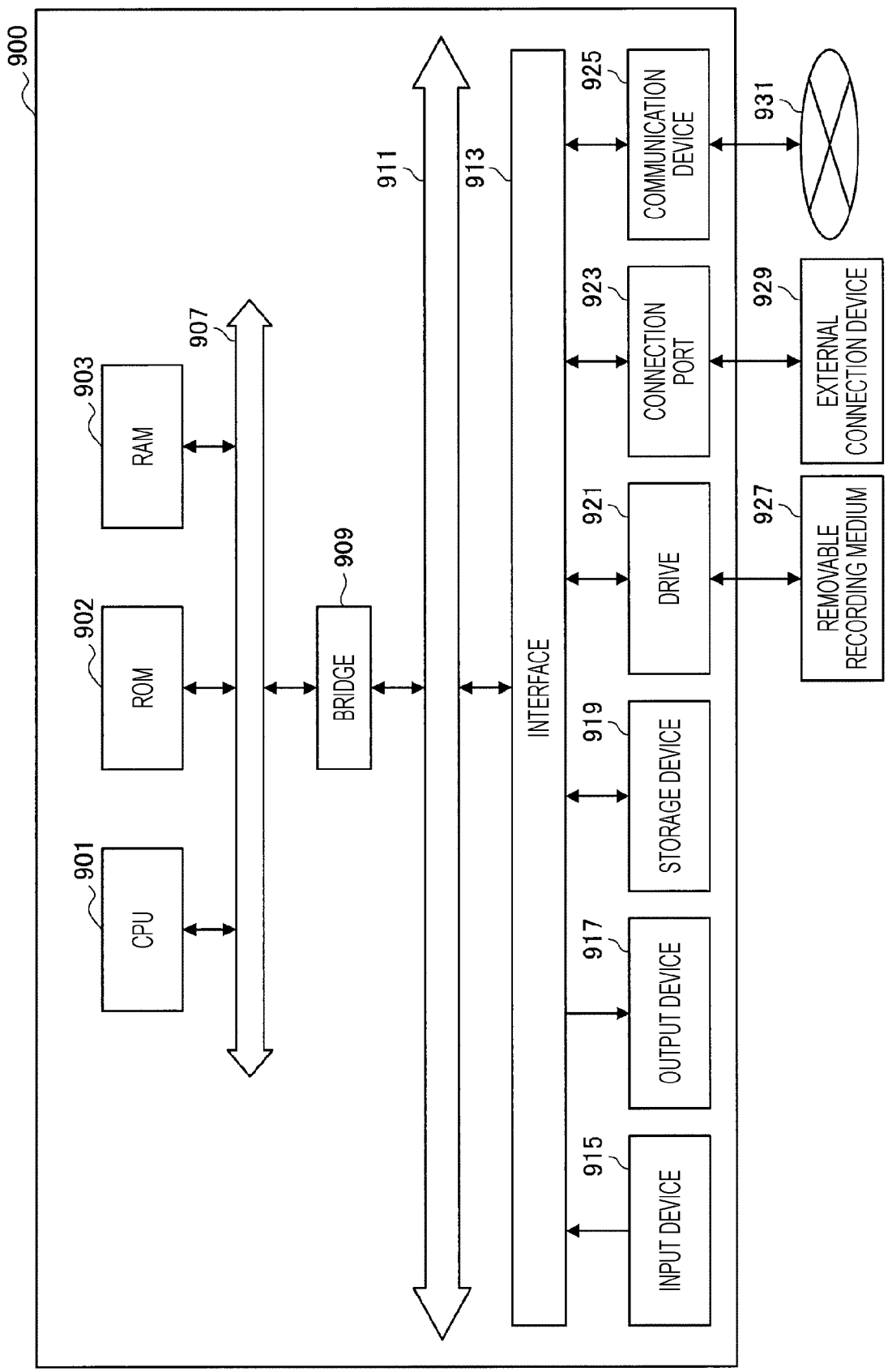
FIG. 13 is a functional block diagram illustrating an exemplary configuration of a hardware configuration of an information processing apparatus included in the medical image processing system according to the embodiment.

Subsequently, an exemplary hardware configuration of an information processing apparatus as the image processing device 230 included in the medical image processing system according to one embodiment of the present disclosure will be described in detail with reference to FIG. 13. FIG. 13 is a functional block diagram illustrating an exemplary configuration of the hardware configuration of the information processing apparatus included in the medical image processing system according to the embodiment of the present disclosure.

An information processing apparatus 900 included in a system according to the present embodiment mainly includes a CPU 901, a ROM 902, and a RAM 903. Furthermore, the information processing apparatus 900 further includes a host bus 907, a bridge 909, an external bus 911, an interface 913, an input device 915, an output device 917, a storage device 919, a drive 921, a connection port 923, and a communication device 925.

The CPU 901 functions as a calculation processing device and a control device and controls all or a part of behaviors in the information processing apparatus 900 according to various programs recorded in the ROM 902, the RAM 903, the storage device 919, or a removable recording medium 927. The ROM 902 stores a program used by the CPU 901, a calculation parameter, and the like. The RAM 903 temporarily stores the program used by the CPU 901, a parameter that appropriately changes when the program is executed, and the like. These are connected to each other by the host bus 907 including an internal bus such as a CPU bus. For example, the image processing unit 231, the estimation unit 237, and the optical characteristics detection unit 238 illustrated in FIG. 8 may be realized by the CPU 901.

The host bus 907 is connected to the external bus 911 such as a Peripheral Component Interconnect/Interface (PCI) bus via the bridge 909. Furthermore, the external bus 911 is connected to the input device 915, the output device 917, the storage device 919, the drive 921, the connection port 923, and the communication device 925 via the interface 913.

The input device 915 is an operation unit operated by a user, for example, a mouse, a keyboard, a touch panel, a button, a switch, a lever, a pedal, or the like. Furthermore, the input device 915 may be, for example, a remote control unit (so-called, remote controller) using infrared rays or other radio waves and may be a mobile phone compatible with an operation of the information processing apparatus 900 or an external connection device 929 such as a PDA. Moreover, the input device 915 includes, for example, an input control circuit that generates an input signal on the basis of information input by a user by using the operation unit and outputs the generated signal to the CPU 901. The user of the information processing apparatus 900 can input various data and give an instruction on a processing operation to the information processing apparatus 900 by operating the input device 915. For example, the input device 293 illustrated in FIG. 8 may be realized by the input device 915.

The output device 917 includes a device that can visually or audibly notifies the user of the acquired information. As such a device, a display device such as a CRT display device, a liquid crystal display device, a plasma display device, an EL display device, a lamp, or the like, an audio output device such as a speaker, a headphone, or the like, a printer device, and the like are exemplified. The output device 917, for example, outputs results obtained by various processing executed by the information processing apparatus 900. Specifically, the display device displays the results obtained by various processing executed by the information processing apparatus 900 as a text or an image. The audio output device converts an audio signal including reproduced audio data, acoustic data, and the like into an analog signal and outputs the converted signal. For example, the display device 291 illustrated in FIG. 8 may be realized by the output device 917.

The storage device 919 is a device for data storage that is configured as an example of a storage unit of the information processing apparatus 900. The storage device 919 includes, for example, a magnetic storage unit device such as a hard disk drive (HDD), a semiconductor storage device, an optical storage device, a magneto-optical storage device, or the like. The storage device 919 stores a program executed by the CPU 901, various data, and the like. For example, the storage unit 239 illustrated in FIG. 8 may be realized by the storage device 919.

The drive 921 is a reader/writer for a recording medium and is built in or externally attached to the information processing apparatus 900. The drive 921 reads information recorded in the removable recording medium 927 such as the attached magnetic disk, optical disk, magneto-optical disk, semiconductor memory, or the like and outputs the information to the RAM 903.

Furthermore, the drive 921 can write a record to the removable recording medium 927 such as the attached magnetic disk, optical disk, magneto-optical disk, semiconductor memory, or the like. The removable recording medium 927 is, for example, DVD media, HD-DVD media, Blu-ray (registered trademark) media, or the like. Furthermore, the removable recording medium 927 may be a CompactFlash (CF) (registered trademark), a flash memory, a secure digital (SD) memory card, or the like. Furthermore, the removable recording medium 927 may be, for example, an Integrated Circuit card (IC card), an electronic apparatus, or the like on which a non-contact IC chip is mounted.

The connection port 923 is a port that is directly connected to the information processing apparatus 900. Examples of the connection port 923 include a universal serial bus (USB) port, an IEEE1394 port, a small computer system interface (SCSI) port, and the like. Other examples of the connection port 923 include an RS-232C port, an optical audio terminal, a High-Definition Multimedia Interface (HDMI) (registered trademark) port, and the like. By connecting the external connection device 929 to the connection port 923, the information processing apparatus 900 directly acquires various data from the external connection device 929 and provides various data to the external connection device 929.

The communication device 925 is a communication interface including, for example, a communication device used to be connected to a communication network (network) 931 and the like. The communication device 925 is, for example, a communication card for a wired or wireless local area network (LAN), the Bluetooth (registered trademark), and a wireless USB (WUSB), and the like. Furthermore, the communication device 925 may be a router for optical communication, a router for Asymmetric Digital Subscriber Line (ADSL), a modem for various communication, and the like. For example, the communication device 925 can exchange a signal and the like with the Internet and other communication devices according to a predetermined protocol, for example, TCP/IP or the like. Furthermore, the communication network 931 connected to the communication device 925 includes a network or the like that is wiredly or wirelessly connected and may be, for example, the Internet, a home LAN, infrared communication, radio wave communication, satellite communication, or the like.

The exemplary hardware configuration that can realize the function of the information processing apparatus 900 included in the system according to the embodiment of the present disclosure has been described above. Each component may be formed by using a general-purpose member or hardware specialized to the function of each component. Therefore, it is possible to appropriately change the hardware configuration to be used according to a technical level at the time of carrying out the present embodiment. Note that, although not illustrated in FIG. 13, various components corresponding to the information processing apparatus 900 included in the system are naturally included.

Note that it is possible to produce a computer program to realize each function of the information processing apparatus 900 included in the information processing system according to the present embodiment described above and implement the produced program on a personal computer and the like. Furthermore, a computer-readable recording medium storing such a computer program can be provided. The recording medium is, for example, a magnetic disk, an optical disk, a magneto-optical disk, a flash memory, and the like. Furthermore, the computer program may be distributed, for example, via a network, without using the recording medium. Furthermore, the number of computers that execute the computer program is not particularly limited. For example, the plurality of computers (for example, a plurality of servers and the like) may execute the computer program in cooperation with each other.

6. Application Example

The technology according to the present disclosure can be applied to various products. For example, the technology according to the present disclosure may be applied to a surgical microscopic system used for a so-called microsurgery performed while magnifying and observing a fine portion of a patient.

Figure 14:
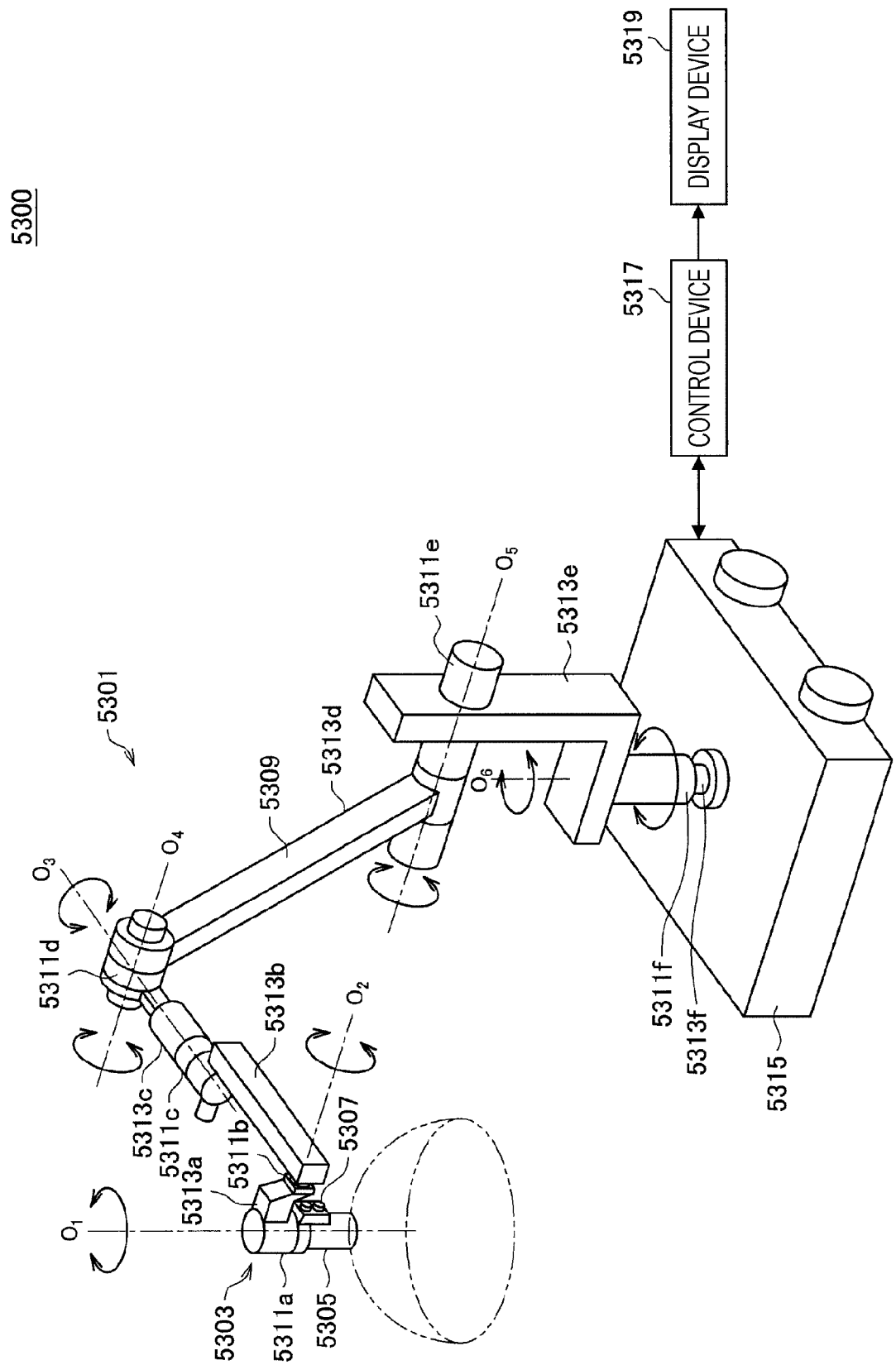
FIG. 14 is a diagram illustrating an example of a schematic configuration of a surgical microscopic system.

FIG. 14 is a diagram illustrating an example of a schematic configuration of a surgical microscopic system 5300 to which the technology according to the present disclosure may be applied. Referring to FIG. 14, the surgical microscopic system 5300 includes a microscopic device 5301, a control device 5317, and a display device 5319. Note that, in the following description of the surgical microscopic system 5300, a "user" means an optional medical staff who uses the surgical microscopic system 5300 such as an operator or an assistant.

The microscopic device 5301 includes a microscopic unit 5303 for magnifying and observing an observation target (surgical site of patient), an arm portion 5309 that supports the microscopic unit 5303 at a front end thereof, and a base portion 5315 that supports a base end of the arm portion 5309.

The microscopic unit 5303 includes a cylindrical portion 5305 having a substantially cylindrical shape, an imaging unit (not illustrated) provided in the cylindrical portion 5305, and an operation unit 5307 provided in a partial region of an outer periphery of the cylindrical portion 5305. The microscopic unit 5303 is an electronic imaging microscopic unit (so-called video-type microscopic unit) that electronically images a captured image by the imaging unit.

On an opening surface at a lower end of the cylindrical portion 5305, cover glass that protects the imaging unit in the cylindrical portion 5305 is provided. Light from the observation target (hereinafter, referred to as observation light) passes through the cover glass and enters the imaging unit in the cylindrical portion 5305. Note that a light source including, for example, a Light Emitting Diode (LED) and the like may be provided in the cylindrical portion 5305, the observation target may be irradiated with the light from the light source through the cover glass at the time of imaging.

The imaging unit includes an optical system that collects the observation light and an imaging element that receives the observation light collected by the optical system. The optical system includes a plurality of lens including a zoom lens and a focus lens in combination with each other, and the optical characteristics are adjusted so that the observation light forms an image on a light receiving surface of the imaging element. The imaging element generates a signal corresponding to the observation light, that is, an image signal corresponding to an observation image by receiving and photoelectrically converting the observation light. As the imaging element, for example, an imaging element, which can perform color-imaging, having a Bayer array is used. The imaging element may be various known imaging elements such as a Complementary Metal Oxide Semiconductor (CMOS) image sensor, a Charge Coupled Device (CCD) image sensor, or the like. The image signal generated by the imaging element is transmitted to the control device 5317 as RAW data. Here, the transmission of the image signal may be preferably performed by optical communication. This is because, since the operator performs a surgery while observing the state of the affected part by using the captured image at the site of surgery, it is required to display a moving image of the surgical site in real time as possible for a safer and more reliable surgery. By transmitting the image signal by the optical communication, it is possible to display a captured image with low latency.

Note that the imaging unit may include a driving mechanism that moves the zoom lens and the focus lens of the optical system along the optical axis. By appropriately moving the zoom lens and the focus lens by the driving mechanism, a magnification of the captured image and a focal length at the time of imaging may be adjusted. Furthermore, the imaging unit may have various functions that may be generally provided in the electronic imaging microscopic unit such as an Auto Exposure (AE) function, an Auto Focus (AF) function, or the like.

Furthermore, the imaging unit may be configured as a so-called single-plate imaging unit including a single imaging element or as a so-called multi-plate imaging unit including a plurality of imaging elements. In a case where the imaging unit has a multi-plate type structure, for example, each imaging element may generate image signals respectively corresponding to R, G, and B, and the image signals may be synthesized to obtain a color image. Alternatively, the imaging unit may include a pair of imaging elements to obtain image signals for the right eye and the left eye coping with stereoscopic (3D display) display. With the 3D display, the operator can more accurately recognize a depth of a living tissue in the operation site. Note that, in a case where the imaging unit has a multi-plate type structure, a plurality of optical systems may be provided corresponding to the imaging elements.

The operation unit 5307 is an input unit that includes, for example, a cross lever, a switch, or the like and receives a user's operation input. For example, the user can input an instruction to change the magnification of the observation target and the focal length to the observation target via the operation unit 5307. By appropriately moving the zoom lens and the focus lens by the driving mechanism of the imaging unit according to the instruction, the magnification and the focal length may be adjusted. Furthermore, for example, the user can input an instruction to switch an operation mode (all-free mode and fixed mode to be described later) of the arm portion 5309 via the operation unit 5307. Note that, in a case where the user tries to move the microscopic unit 5303, a case is assumed in which the user moves the microscopic unit 5303 in a state where the user grips and holds the cylindrical portion 5305. Therefore, it is preferable to provide the operation unit 5307 at a position where the operation unit 5307 is easily operated by fingers in a state where the user grips the cylindrical portion 5305 so that the user can operate the operation unit 5307 while moving the cylindrical portion 5305.

The arm portion 5309 is configured by rotatably coupling a plurality of links (first link 5313a to sixth link 5313f) by a plurality of joint portions (first joint portion 5311a to sixth joint portion 5311f).

The first joint portion 5311a has a substantially columnar shape, and a front end (lower end) of the first joint portion 5311a rotatably supports the upper end of the cylindrical portion 5305 of the microscopic unit 5303 around a rotation axis (first axis $O_1$) parallel to the central axis of the cylindrical portion 5305. Here, the first joint portion 5311a may be configured so that the first axis $O_1$ coincides with the optical axis of the imaging unit of the microscopic unit 5303. With this structure, by rotating the microscopic unit 5303 around the first axis $O_1$, it is possible to change the field of view as rotating the captured image.

The first link 5313a fixedly supports the first joint portion 5311a at the front end. Specifically, the first link 5313a has a bar-like member having a substantially L-like shape and is connected to the first joint portion 5311a so that one side on the front end side extends in a direction orthogonal to the first axis $O_1$ and an end of the one side has contact with the upper end portion of the outer periphery of the first joint portion 5311a. An end of other side on the base end side of the substantially L-like shape of the first link 5313a is connected to the second joint portion 5311b.

The second joint portion 5311b has a substantially columnar shape, and a front end rotatably supports the base end of the first link 5313a around a rotation axis (second axis $O_2$) orthogonal to the first axis $O_1$. The front end of the second link 5313b is fixedly connected to the base end of the second joint portion 5311b.

The second link 5313b is a bar-like member having a substantially L-like shape, and one side on the front end side extends in a direction orthogonal to the second axis $O_2$, and the end of the one side is fixedly connected to the base end of the second joint portion 5311b. The third joint portion 5311c is connected to the other side on the base end side of the substantially L-like shape of the second link 5313b.

The third joint portion 5311c has a substantially columnar shape, and the front end of the third joint portion 5311c rotatably supports the base end of the second link 5313b around a rotation axis (third axis $O_3$) orthogonal to the first axis $O_1$ and the second axis $O_2$. The front end of the third link 5313c is fixedly connected to the base end of the third joint portion 5311c. By rotating the configuration on the front end side including the microscopic unit 5303 around the second axis $O_2$ and the third axis $O_3$, the microscopic unit 5303 can be moved so as to change the position of the microscopic unit 5303 in a horizontal plane. That is, by controlling the rotation around the second axis $O_2$ and the third axis $O_3$, it is possible to move the field of view of the captured image in a plane.

The front end side of the third link 5313c has a substantially columnar shape, and the front end of the columnar shape is fixedly connected to the base end of the third joint portion 5311c so that both components have the substantially the same central axis. The base end side of the third link 5313c has a prismatic shape, and the end of the base end is connected to the fourth joint portion 5311d.

The fourth joint portion 5311d has a substantially columnar shape, and the front end rotatably supports the base end of the third link 5313c around a rotation axis (fourth axis $O_4$) orthogonal to the third axis $O_3$. The front end of the fourth link 5313d is fixedly connected to the base end of the fourth joint portion 5311d.

The fourth link 5313d is a bar-like member that extends in a substantially linearly shape and is fixedly connected to the fourth joint portion 5311d while extending to be orthogonal to the fourth axis $O_4$ so that the end of the front end has contact with a side surface of the substantially columnar shape of the fourth joint portion 5311d. The fifth joint portion 5311e is connected to the base end of the fourth link 5313d.

The fifth joint portion 5311e has a substantially columnar shape, and a front end side rotatably supports the base end of the fourth link 5313d around a rotation axis (fifth axis $O_5$) parallel to the fourth axis $O_4$. The front end of the fifth link 5313e is fixedly connected to the base end of the fifth joint portion 5311e. The fourth axis $O_4$ and the fifth axis $O_5$ are rotation axes that may move the microscopic unit 5303 in the vertical direction. By rotating the configuration on the front end side including the microscopic unit 5303 around the fourth axis $O_4$ and the fifth axis $O_5$, the height of the microscopic unit 5303, that is, a distance between the microscopic unit 5303 and the observation target can be adjusted.

The fifth link 5313e includes a first member that has a substantially L-like shape of which one side extends in the vertical direction and the other side extends in the horizontal direction and a bar-like second member that extends downward in the vertical direction from the portion of the first member extending in the horizontal direction in combination with each other. The base end of the fifth joint portion 5311e is fixedly connected to the vicinity of the upper end of the portion of the first member of the fifth link 5313e that extends in the vertical direction. The base end (lower end) of the second member of the fifth link 5313e is connected to the sixth joint portion 5311f.

The sixth joint portion 5311f has a substantially columnar shape, and a front end side rotatably supports the base end of the fifth link 5313e around a rotation axis (sixth axis $O_6$) parallel to the vertical direction. The front end of the sixth link 5313f is fixedly connected to the base end of the sixth joint portion 5311f.

The sixth link 5313f is a bar-like member that extends in the vertical direction, and the base end thereof is fixedly connected to the upper surface of the base portion 5315.

Rotatable ranges of the first joint portion 5311a to the sixth joint portion 5311f are appropriately set so that the microscopic unit 5303 can achieve a desired movement. With this structure, regarding the arm portion 5309 having the configuration described above, the movement of the microscopic unit 5303 with six degrees of freedom in total including three degrees of translational freedom and three degrees of rotational freedom may be realized. In this way, by configuring the arm portion 5309 so as to realize six degrees of freedom of the movements of the microscopic unit 5303, the position and the posture of the microscopic unit 5303 can be freely controlled in a movable range of the arm portion 5309. Therefore, it is possible to observe the surgical site from any angle, and it is possible to more smoothly perform the surgery.

Note that the illustrated configuration of the arm portion 5309 is merely an example. The number and the shape (length) of the links and the number, the arrangement position, and rotation axis direction, and the like of the joint portions included in the arm portion 5309 may be appropriately designed so as to realize a desired degree of freedom. For example, as described above, to freely move the microscopic unit 5303, it is preferable to configure the arm portion 5309 to have six degrees of freedom. However, the arm portion 5309 may be configured to have a larger degree of freedom (that is, redundant degree of freedom). In a case where the redundant degree of freedom exists, regarding the arm portion 5309, the posture of the arm portion 5309 can be changed in a state where the position and the posture of the microscopic unit 5303 are fixed. Therefore, control that is more convenient for the operator may be realized, for example, control of the posture of the arm portion 5309 so that the arm portion 5309 does not interfere with a field of view of the operator who looks at the display device 5319.

Here, in each of the first joint portion 5311a to the sixth joint portion 5311f, an actuator including a driving mechanism such as a motor, an encoder that detects a rotation angle of each joint portion, and the like may be provided. Then, by appropriately controlling the driving of each actuator provided in each of the first joint portion 5311a to the sixth joint portion 5311f by the control device 5317, the posture of the arm portion 5309, that is, the position and the posture of the microscopic unit 5303 may be controlled. Specifically, the control device 5317 can grasp a current posture of the arm portion 5309 and a current position and posture of the microscopic unit 5303 on the basis of information regarding the rotation angle of each joint portion detected by the encoder. The control device 5317 calculates a control value (for example, rotation angle, generated torque, or the like) relative to each joint portion that realizes the movement of the microscopic unit 5303 in response to the operation input from the user by using the grasped information and makes the driving mechanism of each joint portion drive according to the control value. Note that, at this time, a method of controlling the arm portion 5309 by the control device 5317 is not limited, and various known control method such as force control, position control, or the like may be applied.

For example, by appropriately performing the operation input by the operator via the input device which is not illustrated, the driving of the arm portion 5309 may be controlled by the control device 5317 in response to the operation input, and the position and the posture of the microscopic unit 5303 may be controlled. With this control, after moving the microscopic unit 5303 from a certain position to a certain position, it is possible to fixedly support the microscopic unit 5303 at the position after being moved. Note that, in consideration of the convenience of the operator, it is preferable to apply an input device that is operable even if the operator has a surgical instrument in hands, for example, a foot switch and the like, as the input device. Furthermore, a non-contact operation input may be performed on the basis of gesture detection or line-of-sight detection by using a wearable device or a camera provided in an operation room. With this structure, a user belonging to a clean area can operate a device belonging to an unclean area with a higher degree of freedom. Alternatively, the arm portion 5309 may be operated in a so-called master-slave method. In this case, the arm portion 5309 may be remotely controlled by the user via the input device provided at a place away from the operation room.

Furthermore, in a case where the force control is applied, so-called power assist control may be performed in which the actuators of the first joint portion 5311a to the sixth joint portion 5311f are driven so that the arm portion 5309 receives an external force from the user and is smoothly moved by the external force. With this control, when the user grips the microscopic unit 5303 and directly moves the position of the microscopic unit 5303, the microscopic unit 5303 can be moved with a relatively light force. Therefore, the microscopic unit 5303 can be more intuitively moved by a simpler operation, and the convenience of the user can be improved.

Furthermore, driving of the arm portion 5309 may be controlled to perform a pivot operation. Here, the pivot operation is an operation for moving the microscopic unit 5303 so that the optical axis of the microscopic unit 5303 constantly faces toward a predetermined point (hereinafter, referred to as pivot point) in a space. With the pivot operation, it is possible to observe the same observation position from various directions. Therefore, it is possible to observe the affected part in more detail. Note that, in a case where the focal length of the microscopic unit 5303 cannot be adjusted, it is preferable to perform the pivot operation in a state where a distance between the microscopic unit 5303 and the pivot point is fixed. In this case, it is sufficient that the distance between the microscopic unit 5303 and the pivot point be adjusted to a fixed focal length of the microscopic unit 5303. As a result, the microscopic unit 5303 moves on a hemispherical surface having a radius corresponding to the focal length around the pivot point (schematically illustrated in FIG. 14), and a clearer captured image is obtained even if the observation direction is changed. On the other hand, in a case where the focal length of the microscopic unit 5303 can be adjusted, the pivot operation may be performed in a state where the distance between the microscopic unit 5303 and the pivot point can be changed. In this case, for example, the control device 5317 may calculate the distance between the microscopic unit 5303 and the pivot point on the basis of the information regarding the rotation angle of each joint portion detected by the encoder and automatically adjust the focal length of the microscopic unit 5303 on the basis of the calculation result. Alternatively, in a case where the microscopic unit 5303 has an AF function, the focal length may be automatically adjusted by the AF function each time when the distance between the microscopic unit 5303 and the pivot point is changed by the pivot operation.

Furthermore, a brake that restricts the rotation may be provided in each of the first joint portion 5311a to the sixth joint portion 5311f. The operation of the brake may be controlled by the control device 5317. For example, in a case where it is desired to fix the position and the posture of the microscopic unit 5303, the control device 5317 activates the brake of each joint portion. With this operation, the posture of the arm portion 5309, that is, the position and the posture of the microscopic unit 5303 may be fixed even if the actuator is not driven. Therefore, power consumption can be reduced. In a case where it is desired to move the position and the posture of the microscopic unit 5303, it is sufficient that the control device 5317 release the brake of each joint portion and drive the actuator according to a predetermined control method.

Such an operation of the brake may be performed in response to the operation input by the user via the operation unit 5307. In a case where the user desires to move the position and the posture of the microscopic unit 5303, the user operates the operation unit 5307 and releases the brake of each joint portion. With this operation, an operation mode of the arm portion 5309 shifts to a mode (all-free mode) in which each joint portion can be freely rotated. Furthermore, in a case where the user desires to fix the position and the posture of the microscopic unit 5303, the user operates the operation unit 5307 and activates the brake of each joint portion. With this operation, the operation mode of the arm portion 5309 shifts to a mode (fixed mode) in which the rotation of each joint portion is restricted.

By controlling the operations of the microscopic device 5301 and the display device 5319, the control device 5317 comprehensively controls the operation of the surgical microscopic system 5300. For example, by operating the actuators of the first joint portion 5311*a* to the sixth joint portion 5311*f* according to the predetermined control method, the control device 5317 controls the driving of the arm portion 5309.

Furthermore, for example, by controlling the operations of the brakes of the first joint portion 5311*a* to the sixth joint portion 5311*f*, the control device 5317 changes the operation mode of the arm portion 5309. Furthermore, for example, by executing various signal processing on the image signal obtained by the imaging unit of the microscopic unit 5303 of the microscopic device 5301, the control device 5317 generates image data for display and displays the image data on the display device 5319. As the signal processing, various known signal processing may be executed, for example, development processing (demosaic processing), image quality improvement processing (band emphasis processing, super-resolution processing, Noise reduction (NR) processing, camera shake correction processing, and/or the like), enlargement processing (that is, electronic zoom processing), and/or the like.

Note that the communication between the control device 5317 and the microscopic unit 5303 and the communication between the control device 5317 and the first joint portion 5311*a* to the sixth joint portion 5311*f* may be wired or wireless communication. In a case of the wired communication, communication by electrical signals may be performed, or optical communication may be performed. In this case, a transmission cable used for the wired communication may be configured as an electrical signal cable, an optical fiber, or a composite cable of these according to the communication method. On the other hand, in a case of the wireless communication, it is not necessary not provide the transmission cable in the operation room. Therefore, a case where the transmission cable prevents movements of a medical staff in the operation room can be avoided.

The control device 5317 may be a processor such as a Central Processing Unit (CPU), a Graphics Processing Unit (GPU), or the like or a microcomputer or a control board on which the processor and a storage element such as a memory are mounted. Various functions described above may be realized by operating the processor of the control device 5317 according to a predetermined program. Note that, in the illustrated example, the control device 5317 is provided as a separate device from the microscopic device 5301. However, the control device 5317 may be provided in the base portion 5315 of the microscopic device 5301 and may be integrally configured with the microscopic device 5301. Alternatively, the control device 5317 may include a plurality of devices. For example, a function similar to the control device 5317 may be realized by providing a microcomputer, a control board, and the like in each of the microscopic unit 5303 and the first joint portion 5311*a* to the sixth joint portion 5311*f* of the arm portion 5309 and communicably connecting the provided components.

The display device 5319 is provided in the operation room and displays an image corresponding to the image data generated by the control device 5317 under the control from the control device 5317. That is, an image of the surgical site imaged by the microscopic unit 5303 is displayed on the display device 5319. Note that the display device 5319 may display various information regarding the surgery, for example, patient' body information, information regarding a surgery method, or the like instead of or together with the image of the surgical site. In this case, the display of the display device 5319 may be appropriately switched by the operation by the user. Alternatively, the plurality of display devices 5319 may be provided, and the image of the surgical site and various information regarding the surgery may be displayed on each of the plurality of display devices 5319. Note that, as the display device 5319, various known display devices such as a liquid crystal display device or an Electro Luminescence (EL) display device may be applied.

Figure 15:
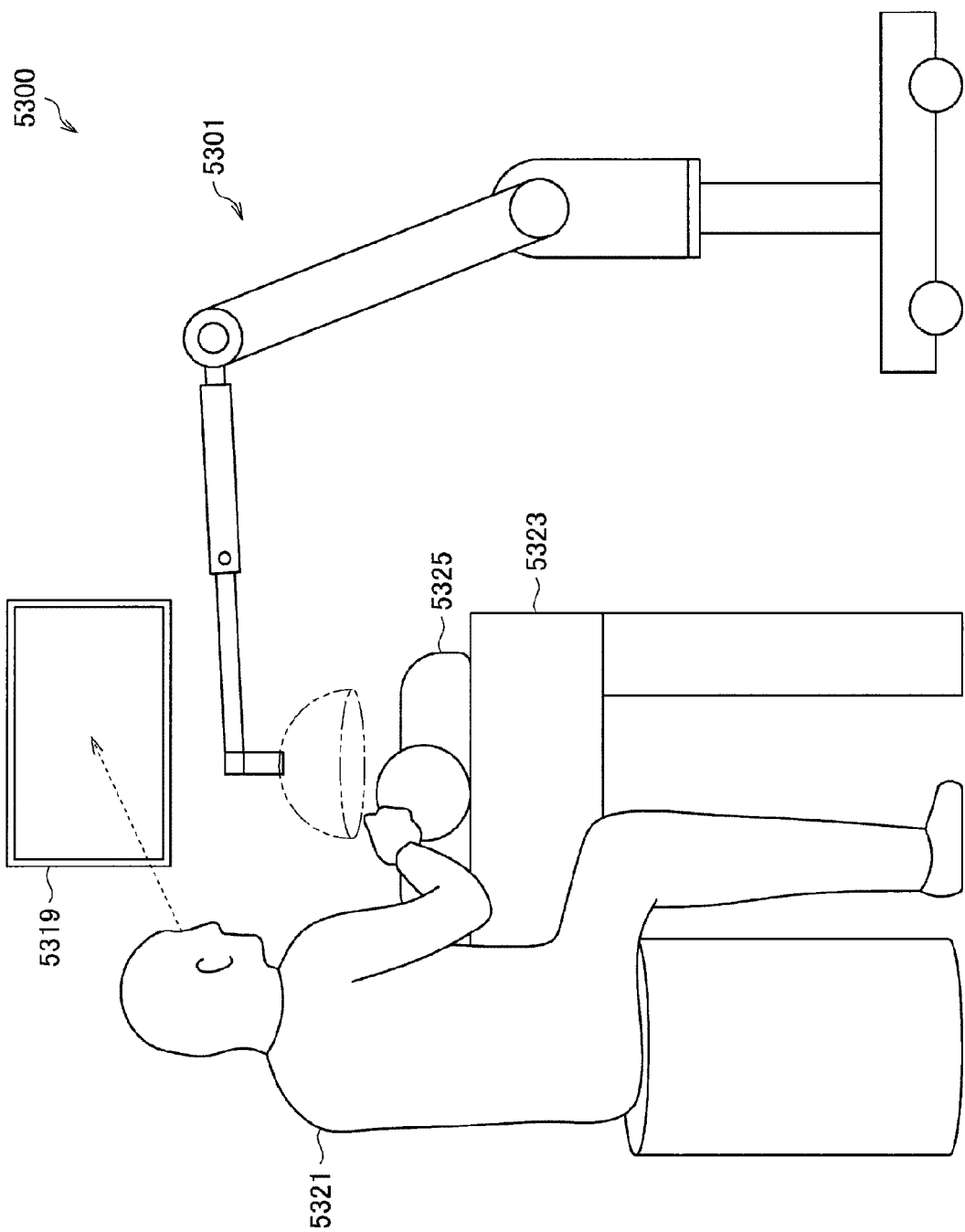
FIG. 15 is a diagram illustrating a state of a surgery using the surgical microscopic system illustrated in FIG. 14.

FIG. 15 is a diagram illustrating a state of a surgery using the surgical microscopic system 5300 illustrated in FIG. 14. FIG. 15 schematically illustrates a state where an operator 5321 performs a surgery on a patient 5325 on a patient bed 5323 by using the surgical microscopic system 5300. Note that, in FIG. 15, for easy illustration, illustration of the control device 5317 of the configuration of the surgical microscopic system 5300 is omitted, and the microscopic device 5301 is illustrated in a simplified manner.

As illustrated in FIG. 15, at the time of surgery, an image of a surgical site imaged by the microscopic device 5301 by using the surgical microscopic system 5300 is magnified and displayed on the display device 5319 provided on a wall of the operation room. The display device 5319 is provided at a position facing the operator 5321, and the operator 5321 executes various processing, for example, removal of the affected part, on the surgical site while observing the state of the surgical site by a video displayed on the display device 5319.

An example of the surgical microscopic system 5300 to which the technology according to the present disclosure may be applied has been described above. Note that, here, the surgical microscopic system 5300 has been described as an example. However, a system to which the technology according to the present disclosure may be applied is not limited to the example. For example, the microscopic device 5301 may function as a support arm device that supports other observation device or other surgical instrument instead of the microscopic unit 5303 at the front end thereof. As the other observation device, for example, an endoscope may be applied. Furthermore, as the other surgical instrument, a forceps, tweezers, a pneumoperitoneum tube for pneumoperitoneum, or an energy treatment instrument that performs incision of tissue by cauterization or blood vessel sealing may be applied, for example. By supporting the observation device and the surgical instrument by the support arm device, it is possible to more stably fix the position and to reduce a load of the medical staff than a case where the medical staff manually supports the observation device and the surgical instrument. The technology according to the present disclosure may be applied to the support arm device that supports the component other than such a microscopic unit.

The technology according to the present disclosure may be preferably applied to the control device 5317 among the components described above. As a specific example, in a case where the autoclave processing is applied to the optical system included in the microscopic unit 5303, the control device 5317 may control the image processing on the image acquired via the microscopic unit 5303 according to the application situation of the autoclave processing. With such a configuration, even in a case where the optical characteristics of the optical system included in the microscopic unit 5303 are changed according to the application of the autoclave processing, the image acquired via the microscopic unit 5303 can be output in a more preferred aspect.

7. Conclusion

As described above, in the medical image processing system according to one embodiment of the present disclosure, the image processing device performs control so as to generate the corrected image by executing the image processing (for example, restoration processing such as deconvolution) on the image obtained by imaging the subject image of the patient acquired via the optical system (for example, endoscope portion) including the birefringent mask. Furthermore, the image processing device acquires the information regarding the application situation of the autoclave processing (for example, autoclave sterilization processing) on the optical system. At this time, the image processing device may acquire the information regarding the application situation of the autoclave processing from the imaging device (that is, medical observation device) that holds the optical system or from the system as the information managed by the in-hospital information management system and the like. Furthermore, the image processing device may acquire the information regarding the application situation of the autoclave processing on the basis of the user input. Then, the image processing device controls the image processing on the image according to the application situation of the autoclave processing on the optical system (in other words, imaging device holding optical system).

With the configuration described above, for example, by repeatedly executing the autoclave sterilization processing on the optical system such as the endoscope, even under a situation in which the optical characteristics (for example, retardation) of the birefringent mask included in the optical system change, it is possible to output the image in a more preferred aspect (for example, output with more preferable image quality). Furthermore, according to the medical image processing system according to the present embodiment, even in a case where the birefringent mask is incorporated in the endoscope and the like and it is difficult to directly detect the change in the optical characteristics of the birefringent mask alone, it is possible to output the image in a more preferred aspect according to the change in the optical characteristics. That is, according to the medical image processing system according to the present embodiment, the control of the expansion of the depth of field using the birefringent mask can be realized in a more preferred aspect.

The preferred embodiments of the present disclosure have been described in detail above with reference to the drawings. However, the technical scope of the present disclosure is not limited to the examples. It is obvious that a person who has normal knowledge in the technical field of the present disclosure can arrive at various variations and modifications in the scope of the technical ideas described in claims. It is understood that the variations and modifications naturally belong to the technical scope of the present disclosure.

Furthermore, the effects described in the present specification are merely illustrative and exemplary and not limited. That is, the technology according to the present disclosure can exhibit other effects obvious to those skilled in the art from the description in the present specification together with or instead of the above described effects.

Furthermore, an application destination of the technology according to the present disclosure is not limited to only the examples described above. That is, in a case where the EDOF technology using the birefringent mask is applied and the autoclave processing is applied to the optical system including the birefringent mask, it is possible to apply the technology according to the present disclosure. Furthermore, in the example described above, the description has been made as mainly assuming a case where the image of the patient (for example, image of surgical site) is captured during the surgery. However, an imaging target may be appropriately changed depending on an application destination of the medical image processing system according to the present embodiment. As a specific example, in a case where the medical image processing system according to the present embodiment is used for examination and analysis, a specimen to be examined or analyzed may be the imaging target (that is, observation target). Therefore, in the present disclosure, it is assumed that a portion described as the "patient" as the target of the imaging and observation includes the "specimen" to be examined or analyzed and may include an idea substantially similar to the "patient" and the "specimen".

Note that the following configuration belongs to the technical scope of the present disclosure.

(1)

A medical image processing apparatus including:

a control unit configured to perform control so as to generate a corrected image by executing image processing on an image obtained by imaging a subject image of a patient acquired via an optical system including a birefringent mask; and an acquisition unit configured to acquire information regarding an application situation of high-pressure steam sterilization processing on the optical system, in which the control unit controls the image processing according to the application situation of the high-pressure steam sterilization processing.

(2)

The medical image processing apparatus according to (1), in which the image processing includes filter processing for adjusting an amount of blur of the image.

(3)

The medical image processing apparatus according to (2), in which the control unit controls the image processing by switching a filter that adjusts the amount of blur according to the application situation.

(4)

The medical image processing apparatus according to (3), in which the control unit generates a new filter on the basis of a plurality of the filters having different filter coefficients according to the application situation and performs control so that the new filter is applied to the image.

(5)

The medical image processing apparatus according to (2), in which the control unit controls the image processing by controlling a coefficient of the filter processing according to the application situation.

(6)

The medical image processing apparatus according to any one of (1) to (5), in which the control unit controls the image processing according to a change in optical characteristics of the optical system estimated according to the application situation of the high-pressure steam sterilization processing.

(7)

The medical image processing apparatus according to (6), in which the optical characteristics include characteristics regarding a refractive index difference of the optical system.

(8)

The medical image processing apparatus according to any one of (1) to (7), further including:

an estimation unit configured to estimate the application situation of the high-pressure steam sterilization processing on the optical system, in which the control unit controls the image processing according to an estimation result of the application situation of the high-pressure steam sterilization processing.

(9)

The medical image processing apparatus according to (8), in which the estimation unit estimates the application situation of the high-pressure steam sterilization processing according to the number of times of high-pressure steam sterilization processing executed on the optical system.

(10)

The medical image processing apparatus according to (9), in which the estimation unit estimates the number of times of the high-pressure steam sterilization processing executed on the optical system on the basis of a detection result of a temperature change in an environment around the optical system by a predetermined temperature sensor.

(11)

The medical image processing apparatus according to (8), in which the estimation unit estimates the application situation of the high-pressure steam sterilization processing according to a time of high-pressure steam sterilization processing executed on the optical system.

(12)

The medical image processing apparatus according to (8), in which the estimation unit estimates the application situation of the high-pressure steam sterilization processing according to a time in which the optical system has been used in the past.

(13)

The medical image processing apparatus according to any one of (1) to (12), in which the control unit controls the image processing, which is scheduled to be applied according to the application situation, according to a predetermined condition.

(14)

The medical image processing apparatus according to (13), in which the predetermined condition includes a condition according to an imaging result of a predetermined subject using the optical system.

(15)

The medical image processing apparatus according to (13) or (14), in which the predetermined condition includes a condition according to a user input.

(16)

The medical image processing apparatus according to (15), in which the predetermined condition includes a condition, according to selection of a user from options regarding an application amount of the image processing, to be presented to the user according to the application situation of the high-pressure steam sterilization processing.

(17)

The medical image processing apparatus according to (16), in which control is performed so that the number of the options to be presented to the user increases as the application amount of the high-pressure steam sterilization processing on the optical system is larger.

(18)

A medical image processing system including:

an imaging device including an optical system that includes a birefringent mask and acquires a subject image of a patient and an imaging unit that captures an image of the subject image; and an image processing device including a control unit that performs control so as to generate a corrected image by executing image processing on the image captured by the imaging unit and an acquisition unit that acquires information regarding an application situation of high-pressure steam sterilization processing on the optical system, in which the control unit controls the image processing according to the application situation of the high-pressure steam sterilization processing.

(19)

The medical image processing system according to (18), in which at least a part of the optical system is configured as an endoscope portion, and the imaging unit captures the subject image acquired by the endoscope portion.

(20)

A driving method of a medical image processing apparatus by a computer, the method including:

performing control so as to generate a corrected image by executing image processing on an image obtained by imaging a subject image of a patient acquired via an optical system including a birefringent mask; and acquiring information regarding an application situation of high-pressure steam sterilization processing on the optical system, in which the image processing is controlled according to the application situation of the high-pressure steam sterilization processing.

REFERENCE SIGNS LIST

200 Medical image processing system
210 Imaging device
211 Optical system
212 Birefringent mask
213 Imaging element
214 Monitoring unit
215 Storage unit
230 Image processing device
231 Image processing unit
232 Development processing unit
233 EDOF processing unit
234 Image quality improvement processing unit
235 Control unit
236 Filter bank
237 Estimation unit
238 Optical characteristics detection unit
239 Storage unit
291 Display device
293 Input device
295 In-hospital information management system

The invention claimed is:

1. A medical image processing apparatus comprising:
circuitry configured to:
generate a corrected image by executing image processing on an image obtained by imaging a subject image of a patient acquired via an optical system including a birefringent mask, the image processing includes filter processing for adjusting an amount of blur of the image;
acquire information regarding an application situation of high-pressure steam sterilization processing on the optical system; and
change a parameter of the filter processing according to the application situation of the high-pressure steam sterilization processing by switching a filter that adjusts the amount of blur according to the application situation.

2. The medical image processing apparatus according to claim 1, wherein the circuitry is further configured to generate a new filter on a basis of a plurality of the filters having different filter coefficients according to the application situation and perform control so that the new filter is applied to the image.

3. The medical image processing apparatus according to claim 1, wherein the circuitry is configured to switch the filter by controlling a coefficient of the filter processing according to the application situation.

4. The medical image processing apparatus according to claim 1, wherein the circuitry is configured to control the image processing according to a change in optical characteristics of the optical system estimated according to the application situation of the high-pressure steam sterilization processing.

5. The medical image processing apparatus according to claim 4, wherein the optical characteristics include characteristics regarding a refractive index difference of the optical system.

6. The medical image processing apparatus according to claim 1, wherein the circuitry is further configured to:
estimate the application situation of the high-pressure steam sterilization processing on the optical system, wherein
control the image processing according to an estimation result of the application situation of the high-pressure steam sterilization processing.

7. The medical image processing apparatus according to claim 6, wherein the circuitry is configured to estimate the application situation of the high-pressure steam sterilization processing according to the number of times of high-pressure steam sterilization processing executed on the optical system.

8. The medical image processing apparatus according to claim 7, wherein the circuitry is configured to estimate the number of times of the high-pressure steam sterilization processing executed on the optical system on a basis of a detection result of a temperature change in an environment around the optical system by a predetermined temperature sensor.

9. The medical image processing apparatus according to claim 6, wherein the circuitry is configured to estimate the application situation of the hi pressure steam sterilization processing according to a time of high-pressure steam sterilization processing executed on the optical system.

10. The medical image processing apparatus according to claim 6, wherein the circuitry is configured to estimate the application situation of the high-pressure steam sterilization processing according to a time in which the optical system has been used in the past.

11. The medical image processing apparatus according to claim 1, wherein the circuitry is configured to control the image processing, which is scheduled to be applied according to the application situation, according to a predetermined condition.

12. The medical image processing apparatus according to claim 11, wherein the predetermined condition includes a condition according to an imaging result of a predetermined subject using the optical system.

13. The medical image processing apparatus according to claim 11, wherein the predetermined condition includes a condition according to a user input.

14. The medical image processing apparatus according to claim 13, wherein the predetermined condition includes a condition, according to selection of a user from options regarding an application amount of the image processing, to be presented to the user according to the application situation of the high-pressure steam sterilization processing.

15. The medical image processing apparatus according to claim 14, wherein the circuitry is configured to perform control so that the number of the options to be presented to the user increases as the application amount of the high-pressure steam sterilization processing on the optical system is larger.

16. A medical image processing system comprising:
a camera including an optical system that includes a birefringent mask and acquires a subject image of a patient and an image sensor that captures an image of the subject image; and
circuitry configured to:
generate a corrected image by executing image processing on the image captured by the image sensor, the image processing includes filter processing for adjusting an amount of blur of the image;
acquire information regarding an application situation of high-pressure steam sterilization processing on the optical system; and
change a parameter of the filter processing according to the application situation of the high-pressure steam sterilization processing by switching a filter that adjusts the amount of blur according to the application situation.

17. The medical image processing system according to claim 16, wherein
at least a part of the optical system is configured as an endoscope portion, and
the image sensor captures the subject image acquired by the endoscope portion.

18. A driving method of a medical image processing apparatus by a computer, the method comprising:
generating a corrected image by executing image processing on an image obtained by imaging a subject image of a patient acquired via an optical system including a birefringent mask, the image processing includes filter processing for adjusting an amount of blur of the image;
acquiring information regarding an application situation of high-pressure steam sterilization processing on the optical system; and
changing a parameter of the filter processing according to the application situation of the high-pressure steam sterilization processing by switching a filter that adjusts the amount of blur according to the application situation.

\* \* \* \* \*